(12) United States Patent
Turner et al.

(10) Patent No.: US 7,585,936 B2
(45) Date of Patent: Sep. 8, 2009

(54) PROTEIN EXPRESSION

(75) Inventors: Mark S. Turner, Brisbane (AU); Philip M. Giffard, Brisbane (AU)

(73) Assignees: Queensland University of Technology (AU); Dairy Australia Limited (AU)

( * ) Notice: Subject to any disclaimer, the term of this patent is extended or adjusted under 35 U.S.C. 154(b) by 0 days.

(21) Appl. No.: 10/576,982

(22) PCT Filed: Oct. 22, 2004

(86) PCT No.: PCT/AU2004/001461

§ 371 (c)(1),
(2), (4) Date: May 1, 2007

(87) PCT Pub. No.: WO2005/040200

PCT Pub. Date: May 6, 2005

(65) Prior Publication Data

US 2007/0276124 A1    Nov. 29, 2007

(30) Foreign Application Priority Data

Oct. 24, 2003  (AU) .............................. 2003905886

(51) Int. Cl.
*C12P 21/06* (2006.01)
*C12P 21/04* (2006.01)
(52) U.S. Cl. ...................... 530/324; 435/69.7; 435/69.1
(58) Field of Classification Search ................ 435/69.1, 435/69.7
See application file for complete search history.

(56) References Cited

FOREIGN PATENT DOCUMENTS

| EP | 0292663 AL | 11/1988 |
|---|---|---|
| WO | WO 2004/096992 A2 | 11/2004 |
| WO | WO 2004/106367 A2 | 12/2004 |

OTHER PUBLICATIONS

Ventura et al 2002 "Identification and characterization of novel surface proteins in *Lactobacillus johnsonii* and *Lactobacillus gasseri*." Appl. Environ. Microbiol. 68:6172-6181.*
Venutura et al 2002 Applied Environ. Microbiol. vol. 68 6172-6181.*
Turner, et al.; "Identification and Characterization of the novel LysM domain-containing surface protein Sep from *Lactobacillus fermentum* BR 11 and its use as a peptide fusion partner in *Lactobacillus* and *Lactococcus*"; Applied & Environmental Microbiology, vol. 70, No. 6, pp. 3673-3680 (Jun. 2004).

Bolotin, et al.; "The Complete Genome Sequence of the Lactic Acid Bacterium *Lactococcus lactis* ssp. *Lactis* IL1403"; Genome Research 11, pp. 731-752 (2001); Cold Spring Harbor Laboratory Press; ISSN 1088-9051/01; www.genome.org.
Accession No. AE016948—*Enterococcus faecalis* V583.
Accession No. AE017205—*Lactobacillus Johnsonii* NCC 533.
Accession No. AL935252—*Lactobacillus plantarum* strain WCFS1 complete genome.
Accession No. AY267208—*Lactobacillus reuteri* Apfl-like protein (Lre0018) gene.
Accession No. Y08498—*L.gasseri* apfA gene.
Bolotin, et al., "The Complete Genome Sequence of the Lactic Acid Bacterium *Lactococcus lactis* ssp. *Lactis* IL1403"; Genome Research, pp. 731-735; 11:731-752 © 2001 Cold Spring Harbor Laboratory Press; ISSN 1088-9051/01; www.genome.org.
Turner, et al., "Identification and Characterization of the Novel LysM Domain-Containing Surface Protein Sep from *Lactobacillus fermentum* BR11 and its Use as a Peptide Fusion Partner in *Lactobacillus* and *Lactococcus*"; Applied & Environmental Microbiology, Jun. 2004, vol. 70, No. 6, pp. 3673-3680, © 2004, American Society for Microbiology; 0099-2240/04.
Ventura, et al., "Identification and Characterization of Novel Surface Proteins in *Lactobacillus johnsonii* and *Lactobacillus gassri*"; Applied & Environmental Microbiology, Dec. 2002, vol. 68, No. 12, pp. 6172-6181; © 2002, American Society for Microbiology; 0099-2240/02.
Aberle et al., "Assembly of the cadherin-catenin complex in vitro with recombinant proteins," *J. Cell Sci.*, (1994) 107:3655-3663.
Jankovic et al., "Contribution of Agregation-Promoting Factor to Maintenance of Cell Shape in *Lactobacillus gasseri* 4B2," *J. Bacteriol.*, (2003) 185(11):3288-3296.
Pfeifer and Rosat, "Probiotics in Alimentation: Clinical Evidence for Their Enhancement of the Natural Immunity of the Gut," *J. Immunol. Methods*, (1999) 42:243-257.
Steen et al., "Cell Wall Attachment of a Widely Distributed Peptidoglycan Binding Domain Is Hindered by Cell Well Constituents," *J. Biol. Chem.*, (2003) 278(26): 23874-23881.

* cited by examiner

*Primary Examiner*—Robert A Zeman
*Assistant Examiner*—Nina Archie
(74) *Attorney, Agent, or Firm*—McDermott Will & Emery LLP

(57) ABSTRACT

The invention provides a peptide having at least about 75% amino acid homology with the sequence shown in SEQ ID No: 2. The peptide of the invention also can include an amino acid homology with the sequence shown in SEQ ID No: 2 corresponding to at least about 80%, at least about 85%, at least about 90% or can include the amino acid sequence shown in SEQ ID No: 2. The peptide of the invention can further include an amino acid sequence selected from the sequences shown in SEQ ID Nos: 1, 3 or 4-6.

9 Claims, 12 Drawing Sheets

Western blot probed with anti-His$_5$ monoclonal antibody.

C = cell-associated extracts
S = supernatant extracts

Figure 8

NH₂-DTIYTVQSGDTLSGISYKFAKDNSMINDLAKKNNIQDINKIFVGQKLIIK-COOH

Figure 9

NH₂-SYTSNASGSEAAAKAWIAGRESGGNYNATNGQYIGKYQLAASYLGGDYSPANQERVADQYVASRYGSWTAAQQFWQANGWY-COOH

Figure 10

NH₂-SDGEIQEYNAQNAANANVANNNTQATQQQTAQAQPQQAQSQANQ-COOH

Figure 11

NH₂-MISKKNFAKVSATLGAVALGVSATATAANA-COOH

Figure 12

NH₂-DTIYTVQSGDTLSGISYKFAKDNSMINDLAKKNNIQDINKIFVGQKLIIKSDGEIQEYNAQNAANANVANNNTQATQQQTAQAQPQQAQSQANQSYTSNASGSEAAAKAWIAGRESGGNYNATNGQYIGKYQLAASYLGGDYSPANQERVADQYVASRYGSWTAAQQFWQANGWY-COOH

Figure 13

NH₂-MISKKNFAKVSATLGAVALGVSATATAANADTIYTVQSGDTLSGISYKFAKDNSMINDLAKKNNIQDINKIFVGQKLIIKSDGEIQEYNAQNAANANVANNNTQATQQQTAQAQPQQAQSQANQSYTSNASGSEAAAKAWIAGRESGGNYNATNGQYIGKYQLAASYLGGDYSPANQERVADQYVASRYGSWTAAQQFWQANGWY-COOH

Figure 14

5'-
ATGATTTCTAAGAAAAACTTTGCTAAAGTATCTGCTACTCTTGGTGCAGTGGC
CTTAGGTGTTAGTGCAACGGCTACTGCTGCTAATGCT-3'

Figure 15

5'-
GACACTATCTACACCGTACAAAGTGGTGACACACTTTCAGGTATTTCTTACAA
ATTTGCTAAAGACAACAGTATGATCAATGATCTTGCTAAGAAGAACAATATT
CAAGATATTAACAAGATTTTTGTTGGTCAAAAGTTAATCATCAAG-3'

Figure 16

5'-
AGCGATGGTGAAATTCAAGAATACAATGCTCAAAATGCAGCTAATGCAAATG
TAGCAAACAACAATACTCAAGCTACACAACAACAAACTGCTCAAGCACAAC
CTCAACAAGCACAAAGCCAAGCTAACCAA-3'

Figure 17

5'-
AGCTACACTTCAAATGCTTCAGGTTCAGAAGCTGCTGCTAAAGCTTGGATTGC
CGGTCGTGAATCAGGTGGTAACTACAACGCCACAAACGGTCAATACATTGGT
AAGTACCAATTAGCTGCATCATACCTTGGTGGTGACTACTCACCAGCTAACC
AAGAACGCGTTGCTGACCAATACGTTGCAAGTCGTTACGGTTCTTGGACTGCT
GCCCAACAATTCTGGCAAGCAAACGGTTGGTACTAA-3'

Figure 18

5'-
GACACTATCTACACCGTACAAAGTGGTGACACACTTTCAGGTATTTCTTACAA
ATTTGCTAAAGACAACAGTATGATCAATGATCTTGCTAAGAAGAACAATATT
CAAGATATTAACAAGATTTTTGTTGGTCAAAAGTTAATCATCAAGAGCGATG
GTGAAATTCAAGAATACAATGCTCAAAATGCAGCTAATGCAAATGTAGCAAA
CAACAATACTCAAGCTACACAACAACAAACTGCTCAAGCACAACCTCAACAA

GCACAAAGCCAAGCTAACCAAAGCTACACTTCAAATGCTTCAGGTTCAGAAG
CTGCTGCTAAAGCTTGGATTGCCGGTCGTGAATCAGGTGGTAACTACAACGC
CACAAACGGTCAATACATTGGTAAGTACCAATTAGCTGCATCATACCTTGGT
GGTGACTACTCACCAGCTAACCAAGAACGCGTTGCTGACCAATACGTTGCAA
GTCGTTACGGTTCTTGGACTGCTGCCCAACAATTCTGGCAAGCAAACGGTTG
GTACTAA-3'

Figure 19

5'-
ATGATTTCTAAGAAAAACTTTGCTAAAGTATCTGCTACTCTTGGTGCAGTGGC
CTTAGGTGTTAGTGCAACGGCTACTGCTGCTAATGCTGACACTATCTACACCG
TACAAAGTGGTGACACACTTTCAGGTATTTCTTACAAATTTGCTAAAGACAAC
AGTATGATCAATGATCTTGCTAAGAAGAACAATATTCAAGATATTAACAAGA
TTTTTGTTGGTCAAAAGTTAATCATCAAGAGCGATGGTGAAATTCAAGAATA
CAATGCTCAAAATGCAGCTAATGCAAATGTAGCAAACAACAATACTCAAGCT
ACACAACAACAAACTGCTCAAGCACAACCTCAACAAGCACAAAGCCAAGCT
AACCAAAGCTACACTTCAAATGCTTCAGGTTCAGAAGCTGCTGCTAAAGCTT
GGATTGCCGGTCGTGAATCAGGTGGTAACTACAACGCCACAAACGGTCAATA
CATTGGTAAGTACCAATTAGCTGCATCATACCTTGGTGGTGACTACTCACCAG
CTAACCAAGAACGCGTTGCTGACCAATACGTTGCAAGTCGTTACGGTTCTTG
GACTGCTGCCCAACAATTCTGGCAAGCAAACGGTTGGTACTAA-3'

Figure 20

5'-
ATGATHWSNAARAARAAYTTYGCNAARGTNWSNGCNACNYTNGGNGCNGTN
GCNYTNGGNGTNWSNGCNACNGCNACNGCNGCNAAYGCN-3'

Figure 21

5'-
GAYACNATHTAYACNGTNCARWSNGGNGAYACNYTNWSNGGNATHWSNTA
YAARTTYGCNAARGAYAAYWSNATGATHAAYGAYYTNGCNAARAARAAYA
AYATHCARGAYATHAAYAARATHTTYGTNGGNCARAARYTNATHATHAAR-3'

Figure 22

5'-
WSNGAYGGNGARATHCARGARTAYAAYGCNCARAAYGCNGCNAAYGCNAAYGTNGCNAAYAAYAAYACNCARGCNACNCARCARCARACNGCNCARGCNCARCCNCARCARGCNCARWSNCARGCNAAYCAR-3'

Figure 23

5'-
WSNTAYACNWSNAAYGCNWSNGGNWSNGARGCNGCNGCNAARGCNTGGATHGCNGGNMGNGARWSNGGNGGNAAYTAYAAYGCNACNAAYGGNCARTAYATHGGNAARTAYCARYTNGCNGCNWSNTAYYTNGGNGGNGAYTAYWSNCCNGCNAAYCARGARMGNGTNGCNGAYCARTAYGTNGCNWSNMGNTAYGGNWSNTGGACNGCNGCNCARCARTTYTGGCARGCNAAYGGNTGGTAY-3'

Figure 24

5'-
GAYACNATHTAYACNGTNCARWSNGGNGAYACNYTNWSNGGNATHWSNTAYAARTTYGCNAARGAYAAYWSNATGATHAAYGAYYTNGCNAARAARAAYAAYATHCARGAYATHAAYAARATHTTYGTNGGNCARAARYTNATHATHAARWSNGAYGGNGARATHCARGARTAYAAYGCNCARAAYGCNGCNAAYGCNAAYGTNGCNAAYAAYAAYACNCARGCNACNCARCARCARACNGCNCARGCNCARCCNCARCARGCNCARWSNCARGCNAAYCARWSNTAYACNWSNAAYGCNWSNGGNWSNGARGCNGCNGCNAARGCNTGGATHGCNGGNMGNGARWSNGGNGGNAAYTAYAAYGCNACNAAYGGNCARTAYATHGGNAARTAYCARYTNGCNGCNWSNTAYYTNGGNGGNGAYTAYWSNCCNGCNAAYCARGARMGNGTNGCNGAYCARTAYGTNGCNWSNMGNTAYGGNWSNTGGACNGCNGCNCARCARTTYTGGCARGCNAAYGGNTGGTAY-3'

Figure 25

5'-
ATGATHWSNAARAARAAYTTYGCNAARGTNWSNGCNACNYTNGGNGCNGTNGCNYTNGGNGTNWSNGCNACNGCNACNGCNGCNAAYGCNGAYACNATHTAY

ACNGTNCARWSNGGNGAYACNYTNWSNGGNATHWSNTAYAARTTYGCNAA
RGAYAAYWSNATGATHAAYGAYYTNGCNAARAARAAYAAYATHCARGAYA
THAAYAARATHTTYGTNGGNCARAARYTNATHATHAARWSNGAYGGNGARA
THCARGARTAYAAYGCNCARAAYGCNGCNAAYGCNAAYGTNGCNAAYAAYA
AYACNCARGCNACNCARCARCARACNGCNCARGCNCARCCNCARCARGCNC
ARWSNCARGCNAAYCARWSNTAYACNWSNAAYGCNWSNGGNWSNGARGCN
GCNGCNAARGCNTGGATHGCNGGNMGNGARWSNGGNGGNAAYTAYAAYGC
NACNAAYGGNCARTAYATHGGNAARTAYCARYTNGCNGCNWSNTAYYTNGG
NGGNGAYTAYWSNCCNGCNAAYCARGARMGNGTNGCNGAYCARTAYGTNG
CNWSNMGNTAYGGNWSNTGGACNGCNGCNCARCARTTYTGGCARGCNAAY
GGNTGGTAY-3'

Figure 26

TAAAGATAGTTATAAACGGAAAATAAAGGGCGGTTTTGGAGCAAATA
TGAAATTTTTGCGAAGAAATCAGCTTTTTTATTTATTTTTTTATAAATCATCT
GTAAAAGTTATGCAAACCGAAAACGCAACCCGCACAAGGAATTAGCCGATT
ATGACTATAATATTTTAAAAGCTATATTACAAAAAGCAAACGGAGAGTAGTA
AATAGAAAT

-35 -10/-35 -10

GGTGCTGTTACAGCTTTGTAATATTAAGAGTGTAGTATATAGGG*TG*TT
GAAACGGAAAAGATAATT*TG*CTAAATAATAAAGGATGGTTATTTAATTT

AATAAATAAGATTAATCAATTTTATTGCGAGACTGATGGAATATTATT
TCCTTCTGTCTCGCTTTTTTGGGCTAATATGTTATAATGGTAGTACTTCTTATG
GGGATGTTTATGGATTCGACAGGTATAGGTCGAGTTTCAACTGCGTTT

SEQUENCE LISTING

```
<160> NUMBER OF SEQ ID NOS: 20

<210> SEQ ID NO 1
<211> LENGTH: 50
<212> TYPE: PRT
<213> ORGANISM: Lactobacillus fermentum

<400> SEQUENCE: 1

Asp Thr Ile Tyr Thr Val Gln Ser Gly Asp Thr Leu Ser Gly Ile Ser
1               5                   10                  15

Tyr Lys Phe Ala Lys Asp Asn Ser Met Ile Asn Asp Leu Ala Lys Lys
            20                  25                  30

Asn Asn Ile Gln Asp Ile Asn Lys Ile Phe Val Gly Gln Lys Leu Ile
```

```
                35                  40                  45
Ile Lys
    50

<210> SEQ ID NO 2
<211> LENGTH: 81
<212> TYPE: PRT
<213> ORGANISM: Lactobacillus fermentum

<400> SEQUENCE: 2

Ser Tyr Thr Ser Asn Ala Ser Gly Ser Glu Ala Ala Lys Ala Trp
1               5                   10                  15

Ile Ala Gly Arg Glu Ser Gly Gly Asn Tyr Asn Ala Thr Asn Gly Gln
            20                  25                  30

Tyr Ile Gly Lys Tyr Gln Leu Ala Ser Tyr Leu Gly Gly Asp Tyr
            35                  40                  45

Ser Pro Ala Asn Gln Glu Arg Val Ala Asp Gln Tyr Val Ala Ser Arg
    50                  55                  60

Tyr Gly Ser Trp Thr Ala Ala Gln Gln Phe Trp Gln Ala Asn Gly Trp
65                  70                  75                  80

Tyr

<210> SEQ ID NO 3
<211> LENGTH: 44
<212> TYPE: PRT
<213> ORGANISM: Lactobacillus fermentum

<400> SEQUENCE: 3

Ser Asp Gly Glu Ile Gln Glu Tyr Asn Ala Gln Asn Ala Ala Asn Ala
1               5                   10                  15

Asn Val Ala Asn Asn Thr Gln Ala Thr Gln Gln Thr Ala Gln
            20                  25                  30

Ala Gln Pro Gln Gln Ala Gln Ser Gln Ala Asn Gln
            35                  40

<210> SEQ ID NO 4
<211> LENGTH: 30
<212> TYPE: PRT
<213> ORGANISM: Lactobacillus fermentum

<400> SEQUENCE: 4

Met Ile Ser Lys Lys Asn Phe Ala Lys Val Ser Ala Thr Leu Gly Ala
1               5                   10                  15

Val Ala Leu Gly Val Ser Ala Thr Ala Ala Asn Ala
            20                  25                  30

<210> SEQ ID NO 5
<211> LENGTH: 175
<212> TYPE: PRT
<213> ORGANISM: Lactobacillus fermentum

<400> SEQUENCE: 5

Asp Thr Ile Tyr Thr Val Gln Ser Gly Asp Thr Leu Ser Gly Ile Ser
1               5                   10                  15

Tyr Lys Phe Ala Lys Asp Asn Ser Met Ile Asn Asp Leu Ala Lys Lys
            20                  25                  30

Asn Asn Ile Gln Asp Ile Asn Lys Ile Phe Val Gly Gln Lys Leu Ile
            35                  40                  45

Ile Lys Ser Asp Gly Glu Ile Gln Glu Tyr Asn Ala Gln Asn Ala Ala
```

```
            50                  55                  60
Asn Ala Asn Val Ala Asn Asn Thr Gln Ala Thr Gln Gln Gln Thr
 65                  70                  75                  80

Ala Gln Ala Gln Pro Gln Gln Ala Gln Ser Gln Ala Asn Gln Ser Tyr
                 85                  90                  95

Thr Ser Asn Ala Ser Gly Ser Glu Ala Ala Lys Ala Trp Ile Ala
            100                 105                 110

Gly Arg Glu Ser Gly Gly Asn Tyr Asn Ala Thr Asn Gly Gln Tyr Ile
            115                 120                 125

Gly Lys Tyr Gln Leu Ala Ala Ser Tyr Leu Gly Gly Asp Tyr Ser Pro
130                 135                 140

Ala Asn Gln Glu Arg Val Ala Asp Gln Tyr Val Ala Ser Arg Tyr Gly
145                 150                 155                 160

Ser Trp Thr Ala Ala Gln Gln Phe Trp Gln Ala Asn Gly Trp Tyr
            165                 170                 175

<210> SEQ ID NO 6
<211> LENGTH: 205
<212> TYPE: PRT
<213> ORGANISM: Lactobacillus fermentum

<400> SEQUENCE: 6

Met Ile Ser Lys Lys Asn Phe Ala Lys Val Ser Ala Thr Leu Gly Ala
  1               5                  10                  15

Val Ala Leu Gly Val Ser Ala Thr Ala Ala Asn Ala Asp Thr
             20                  25                  30

Ile Tyr Thr Val Gln Ser Gly Asp Thr Leu Ser Gly Ile Ser Tyr Lys
             35                  40                  45

Phe Ala Lys Asp Asn Ser Met Ile Asn Asp Leu Ala Lys Lys Asn Asn
         50                  55                  60

Ile Gln Asp Ile Asn Lys Ile Phe Val Gly Gln Lys Leu Ile Ile Lys
 65                  70                  75                  80

Ser Asp Gly Glu Ile Gln Glu Tyr Asn Ala Gln Asn Ala Ala Asn Ala
                 85                  90                  95

Asn Val Ala Asn Asn Thr Gln Ala Thr Gln Gln Gln Thr Ala Gln
            100                 105                 110

Ala Gln Pro Gln Gln Ala Gln Ser Gln Ala Asn Gln Ser Tyr Thr Ser
            115                 120                 125

Asn Ala Ser Gly Ser Glu Ala Ala Lys Ala Trp Ile Ala Gly Arg
130                 135                 140

Glu Ser Gly Gly Asn Tyr Asn Ala Thr Asn Gly Gln Tyr Ile Gly Lys
145                 150                 155                 160

Tyr Gln Leu Ala Ala Ser Tyr Leu Gly Gly Asp Tyr Ser Pro Ala Asn
            165                 170                 175

Gln Glu Arg Val Ala Asp Gln Tyr Val Ala Ser Arg Tyr Gly Ser Trp
            180                 185                 190

Thr Ala Ala Gln Gln Phe Trp Gln Ala Asn Gly Trp Tyr
            195                 200                 205

<210> SEQ ID NO 7
<211> LENGTH: 90
<212> TYPE: DNA
<213> ORGANISM: Lactobacillus fermentum

<400> SEQUENCE: 7
atgatttcta agaaaaactt tgctaaagta tctgctactc ttggtgcagt ggccttaggt    60
```

```
<210> SEQ ID NO 8
<211> LENGTH: 150
<212> TYPE: DNA
<213> ORGANISM: Lactobacillus fermentum

<400> SEQUENCE: 8
gacactatct acaccgtaca aagtggtgac acactttcag gtatttctta caaatttgct    60
aaagacaaca gtatgatcaa tgatcttgct aagaagaaca atattcaaga tattaacaag   120
atttttgttg gtcaaaagtt aatcatcaag                                    150

<210> SEQ ID NO 9
<211> LENGTH: 132
<212> TYPE: DNA
<213> ORGANISM: Lactobacillus fermentum

<400> SEQUENCE: 9
agcgatggtg aaattcaaga atacaatgct caaaatgcag ctaatgcaaa tgtagcaaac    60
aacaatactc aagctacaca acaacaaact gctcaagcac aacctcaaca agcacaaagc   120
caagctaacc aa                                                       132

<210> SEQ ID NO 10
<211> LENGTH: 246
<212> TYPE: DNA
<213> ORGANISM: Lactobacillus fermentum

<400> SEQUENCE: 10
agctacactt caaatgcttc aggttcagaa gctgctgcta aagcttggat tgccggtcgt    60
gaatcaggtg gtaactacaa cgccacaaac ggtcaataca ttggtaagta ccaattagct   120
gcatcatacc ttggtggtga ctactcacca gctaaccaag aacgcgttgc tgaccaatac   180
gttgcaagtc gttacggttc ttggactgct gcccaacaat tctggcaagc aaacggttgg   240
tactaa                                                              246

<210> SEQ ID NO 11
<211> LENGTH: 528
<212> TYPE: DNA
<213> ORGANISM: Lactobacillus fermentum

<400> SEQUENCE: 11
gacactatct acaccgtaca aagtggtgac acactttcag gtatttctta caaatttgct    60
aaagacaaca gtatgatcaa tgatcttgct aagaagaaca atattcaaga tattaacaag   120
atttttgttg gtcaaaagtt aatcatcaag agcgatggtg aaattcaaga atacaatgct   180
caaaatgcag ctaatgcaaa tgtagcaaac aacaatactc aagctacaca acaacaaact   240
gctcaagcac aacctcaaca agcacaaagc caagctaacc aaagctacac ttcaaatgct   300
tcaggttcag aagctgctgc taaagcttgg attgccggtc gtgaatcagg tggtaactac   360
aacgccacaa acggtcaata cattggtaag taccaattag ctgcatcata ccttggtggt   420
gactactcac cagctaacca agaacgcgtt gctgaccaat acgttgcaag tcgttacggt   480
tcttggactg ctgcccaaca attctggcaa gcaaacggtt ggtactaa                528

<210> SEQ ID NO 12
<211> LENGTH: 618
<212> TYPE: DNA
```

<213> ORGANISM: Lactobacillus fermentum

<400> SEQUENCE: 12

```
atgatttcta agaaaaactt tgctaaagta tctgctactc ttggtgcagt ggccttaggt      60
gttagtgcaa cggctactgc tgctaatgct gacactatct acaccgtaca aagtggtgac    120
acactttcag gtatttctta caaatttgct aaagacaaca gtatgatcaa tgatcttgct    180
aagaagaaca atattcaaga tattaacaag attttgttg gtcaaaagtt aatcatcaag     240
agcgatggtg aaattcaaga atacaatgct caaaatgcag ctaatgcaaa tgtagcaaac    300
aacaatactc aagctacaca acaacaaact gctcaagcac aacctcaaca agcacaaagc    360
caagctaacc aaagctacac ttcaaatgct tcaggttcag aagctgctgc taaagcttgg    420
attgccggtc gtgaatcagg tggtaactac aacgccacaa acggtcaata cattggtaag    480
taccaattag ctgcatcata ccttggtggt gactactcac cagctaacca gaacgcgtt    540
gctgaccaat acgttgcaag tcgttacggt tcttggactg ctgcccaaca attctggcaa    600
gcaaacggtt ggtactaa                                                   618
```

<210> SEQ ID NO 13
<211> LENGTH: 90
<212> TYPE: DNA
<213> ORGANISM: Lactobacillus fermentum
<220> FEATURE:
<221> NAME/KEY: misc_feature
<222> LOCATION: (9)..(9)
<223> OTHER INFORMATION: any nucleotide
<220> FEATURE:
<221> NAME/KEY: misc_feature
<222> LOCATION: (24)..(24)
<223> OTHER INFORMATION: any nucleotide
<220> FEATURE:
<221> NAME/KEY: misc_feature
<222> LOCATION: (30)..(30)
<223> OTHER INFORMATION: any nucleotide
<220> FEATURE:
<221> NAME/KEY: misc_feature
<222> LOCATION: (33)..(33)
<223> OTHER INFORMATION: any nucleotide
<220> FEATURE:
<221> NAME/KEY: misc_feature
<222> LOCATION: (36)..(36)
<223> OTHER INFORMATION: any nucleotide
<220> FEATURE:
<221> NAME/KEY: misc_feature
<222> LOCATION: (39)..(39)
<223> OTHER INFORMATION: any nucleotide
<220> FEATURE:
<221> NAME/KEY: misc_feature
<222> LOCATION: (42)..(42)
<223> OTHER INFORMATION: any nucleotide
<220> FEATURE:
<221> NAME/KEY: misc_feature
<222> LOCATION: (45)..(45)
<223> OTHER INFORMATION: any nucleotide
<220> FEATURE:
<221> NAME/KEY: misc_feature
<222> LOCATION: (48)..(48)
<223> OTHER INFORMATION: any nucleotide
<220> FEATURE:
<221> NAME/KEY: misc_feature
<222> LOCATION: (51)..(51)
<223> OTHER INFORMATION: any nucleotide
<220> FEATURE:
<221> NAME/KEY: misc_feature
<222> LOCATION: (54)..(54)
<223> OTHER INFORMATION: any nucleotide
<220> FEATURE:
<221> NAME/KEY: misc_feature
<222> LOCATION: (57)..(57)
<223> OTHER INFORMATION: any nucleotide

```
<220> FEATURE:
<221> NAME/KEY: misc_feature
<222> LOCATION: (60)..(60)
<223> OTHER INFORMATION: any nucleotide
<220> FEATURE:
<221> NAME/KEY: misc_feature
<222> LOCATION: (63)..(63)
<223> OTHER INFORMATION: any nucleotide
<220> FEATURE:
<221> NAME/KEY: misc_feature
<222> LOCATION: (66)..(66)
<223> OTHER INFORMATION: any nucleotide
<220> FEATURE:
<221> NAME/KEY: misc_feature
<222> LOCATION: (69)..(69)
<223> OTHER INFORMATION: any nucleotide
<220> FEATURE:
<221> NAME/KEY: misc_feature
<222> LOCATION: (72)..(72)
<223> OTHER INFORMATION: any nucleotide
<220> FEATURE:
<221> NAME/KEY: misc_feature
<222> LOCATION: (75)..(75)
<223> OTHER INFORMATION: any nucleotide
<220> FEATURE:
<221> NAME/KEY: misc_feature
<222> LOCATION: (78)..(78)
<223> OTHER INFORMATION: any nucleotide
<220> FEATURE:
<221> NAME/KEY: misc_feature
<222> LOCATION: (81)..(81)
<223> OTHER INFORMATION: any nucleotide
<220> FEATURE:
<221> NAME/KEY: misc_feature
<222> LOCATION: (84)..(84)
<223> OTHER INFORMATION: any nucleotide
<220> FEATURE:
<221> NAME/KEY: misc_feature
<222> LOCATION: (90)..(90)
<223> OTHER INFORMATION: any nucleotide

<400> SEQUENCE: 13
atgathwsna araaraaytt ygcnaargtn wsngcnacny tnggngcngt ngcnytnggn    60
gtnwsngcna cngcnacngc ngcnaaygcn                                    90

<210> SEQ ID NO 14
<211> LENGTH: 150
<212> TYPE: DNA
<213> ORGANISM: Lactobacillus fermentum
<220> FEATURE:
<221> NAME/KEY: misc_feature
<222> LOCATION: (6)..(6)
<223> OTHER INFORMATION: any nucleotide
<220> FEATURE:
<221> NAME/KEY: misc_feature
<222> LOCATION: (15)..(15)
<223> OTHER INFORMATION: any nucleotide
<220> FEATURE:
<221> NAME/KEY: misc_feature
<222> LOCATION: (18)..(18)
<223> OTHER INFORMATION: any nucleotide
<220> FEATURE:
<221> NAME/KEY: misc_feature
<222> LOCATION: (24)..(24)
<223> OTHER INFORMATION: any nucleotide
<220> FEATURE:
<221> NAME/KEY: misc_feature
<222> LOCATION: (27)..(27)
<223> OTHER INFORMATION: any nucleotide
<220> FEATURE:
<221> NAME/KEY: misc_feature
<222> LOCATION: (33)..(33)
<223> OTHER INFORMATION: any nucleotide
<220> FEATURE:
<221> NAME/KEY: misc_feature
<222> LOCATION: (36)..(36)
```

```
<223> OTHER INFORMATION: any nucleotide
<220> FEATURE:
<221> NAME/KEY: misc_feature
<222> LOCATION: (39)..(39)
<223> OTHER INFORMATION: any nucleotide
<220> FEATURE:
<221> NAME/KEY: misc_feature
<222> LOCATION: (42)..(42)
<223> OTHER INFORMATION: any nucleotide
<220> FEATURE:
<221> NAME/KEY: misc_feature
<222> LOCATION: (48)..(48)
<223> OTHER INFORMATION: any nucleotide
<220> FEATURE:
<221> NAME/KEY: misc_feature
<222> LOCATION: (60)..(60)
<223> OTHER INFORMATION: any nucleotide
<220> FEATURE:
<221> NAME/KEY: misc_feature
<222> LOCATION: (72)..(72)
<223> OTHER INFORMATION: any nucleotide
<220> FEATURE:
<221> NAME/KEY: misc_feature
<222> LOCATION: (87)..(87)
<223> OTHER INFORMATION: any nucleotide
<220> FEATURE:
<221> NAME/KEY: misc_feature
<222> LOCATION: (90)..(90)
<223> OTHER INFORMATION: any nucleotide
<220> FEATURE:
<221> NAME/KEY: misc_feature
<222> LOCATION: (129)..(129)
<223> OTHER INFORMATION: any nucleotide
<220> FEATURE:
<221> NAME/KEY: misc_feature
<222> LOCATION: (132)..(132)
<223> OTHER INFORMATION: any nucleotide
<220> FEATURE:
<221> NAME/KEY: misc_feature
<222> LOCATION: (141)..(141)
<223> OTHER INFORMATION: any nucleotide

<400> SEQUENCE: 14
gayacnatht ayacngtnca rwsnggngay acnytnwsng gnathwsnta yaarttygcn      60
aargayaayw snatgathaa ygayytngcn aaraaraaya ayathcarga yathaayaar     120
athttygtng gncaraaryt nathathaar                                     150

<210> SEQ ID NO 15
<211> LENGTH: 132
<212> TYPE: DNA
<213> ORGANISM: Lactobacillus fermentum
<220> FEATURE:
<221> NAME/KEY: misc_feature
<222> LOCATION: (3)..(3)
<223> OTHER INFORMATION: any nucleotide
<220> FEATURE:
<221> NAME/KEY: misc_feature
<222> LOCATION: (9)..(9)
<223> OTHER INFORMATION: any nucleotide
<220> FEATURE:
<221> NAME/KEY: misc_feature
<222> LOCATION: (30)..(30)
<223> OTHER INFORMATION: any nucleotide
<220> FEATURE:
<221> NAME/KEY: misc_feature
<222> LOCATION: (39)..(39)
<223> OTHER INFORMATION: any nucleotide
<220> FEATURE:
<221> NAME/KEY: misc_feature
<222> LOCATION: (42)..(42)
<223> OTHER INFORMATION: any nucleotide
<220> FEATURE:
<221> NAME/KEY: misc_feature
<222> LOCATION: (48)..(48)
<223> OTHER INFORMATION: any nucleotide
```

<220> FEATURE:
<221> NAME/KEY: misc_feature
<222> LOCATION: (54)..(54)
<223> OTHER INFORMATION: any nucleotide
<220> FEATURE:
<221> NAME/KEY: misc_feature
<222> LOCATION: (57)..(57)
<223> OTHER INFORMATION: any nucleotide
<220> FEATURE:
<221> NAME/KEY: misc_feature
<222> LOCATION: (69)..(69)
<223> OTHER INFORMATION: any nucleotide
<220> FEATURE:
<221> NAME/KEY: misc_feature
<222> LOCATION: (75)..(75)
<223> OTHER INFORMATION: any nucleotide
<220> FEATURE:
<221> NAME/KEY: misc_feature
<222> LOCATION: (78)..(78)
<223> OTHER INFORMATION: any nucleotide
<220> FEATURE:
<221> NAME/KEY: misc_feature
<222> LOCATION: (90)..(90)
<223> OTHER INFORMATION: any nucleotide
<220> FEATURE:
<221> NAME/KEY: misc_feature
<222> LOCATION: (93)..(93)
<223> OTHER INFORMATION: any nucleotide
<220> FEATURE:
<221> NAME/KEY: misc_feature
<222> LOCATION: (99)..(99)
<223> OTHER INFORMATION: any nucleotide
<220> FEATURE:
<221> NAME/KEY: misc_feature
<222> LOCATION: (105)..(105)
<223> OTHER INFORMATION: any nucleotide
<220> FEATURE:
<221> NAME/KEY: misc_feature
<222> LOCATION: (114)..(114)
<223> OTHER INFORMATION: any nucleotide
<220> FEATURE:
<221> NAME/KEY: misc_feature
<222> LOCATION: (120)..(120)
<223> OTHER INFORMATION: any nucleotide
<220> FEATURE:
<221> NAME/KEY: misc_feature
<222> LOCATION: (126)..(126)
<223> OTHER INFORMATION: any nucleotide

<400> SEQUENCE: 15
wsngayggng arathcarga rtayaaygcn caraaygcng cnaaygcnaa ygtngcnaay    60
aayaayacnc argcnacnca rcarcaracn gcncargcnc arccncarca rgcncarwsn   120
cargcnaayc ar                                                      132

<210> SEQ ID NO 16
<211> LENGTH: 243
<212> TYPE: DNA
<213> ORGANISM: Lactobacillus fermentum
<220> FEATURE:
<221> NAME/KEY: misc_feature
<222> LOCATION: (3)..(3)
<223> OTHER INFORMATION: any nucleotide
<220> FEATURE:
<221> NAME/KEY: misc_feature
<222> LOCATION: (9)..(9)
<223> OTHER INFORMATION: any nucleotide
<220> FEATURE:
<221> NAME/KEY: misc_feature
<222> LOCATION: (12)..(12)
<223> OTHER INFORMATION: any nucleotide
<220> FEATURE:
<221> NAME/KEY: misc_feature
<222> LOCATION: (18)..(18)
<223> OTHER INFORMATION: any nucleotide
<220> FEATURE:

```
<221> NAME/KEY: misc_feature
<222> LOCATION: (21)..(21)
<223> OTHER INFORMATION: any nucleotide
<220> FEATURE:
<221> NAME/KEY: misc_feature
<222> LOCATION: (24)..(24)
<223> OTHER INFORMATION: any nucleotide
<220> FEATURE:
<221> NAME/KEY: misc_feature
<222> LOCATION: (27)..(27)
<223> OTHER INFORMATION: any nucleotide
<220> FEATURE:
<221> NAME/KEY: misc_feature
<222> LOCATION: (33)..(33)
<223> OTHER INFORMATION: any nucleotide
<220> FEATURE:
<221> NAME/KEY: misc_feature
<222> LOCATION: (36)..(36)
<223> OTHER INFORMATION: any nucleotide
<220> FEATURE:
<221> NAME/KEY: misc_feature
<222> LOCATION: (39)..(39)
<223> OTHER INFORMATION: any nucleotide
<220> FEATURE:
<221> NAME/KEY: misc_feature
<222> LOCATION: (45)..(45)
<223> OTHER INFORMATION: any nucleotide
<220> FEATURE:
<221> NAME/KEY: misc_feature
<222> LOCATION: (54)..(54)
<223> OTHER INFORMATION: any nucleotide
<220> FEATURE:
<221> NAME/KEY: misc_feature
<222> LOCATION: (57)..(57)
<223> OTHER INFORMATION: any nucleotide
<220> FEATURE:
<221> NAME/KEY: misc_feature
<222> LOCATION: (60)..(60)
<223> OTHER INFORMATION: any nucleotide
<220> FEATURE:
<221> NAME/KEY: misc_feature
<222> LOCATION: (66)..(66)
<223> OTHER INFORMATION: any nucleotide
<220> FEATURE:
<221> NAME/KEY: misc_feature
<222> LOCATION: (69)..(69)
<223> OTHER INFORMATION: any nucleotide
<220> FEATURE:
<221> NAME/KEY: misc_feature
<222> LOCATION: (72)..(72)
<223> OTHER INFORMATION: any nucleotide
<220> FEATURE:
<221> NAME/KEY: misc_feature
<222> LOCATION: (84)..(84)
<223> OTHER INFORMATION: any nucleotide
<220> FEATURE:
<221> NAME/KEY: misc_feature
<222> LOCATION: (87)..(87)
<223> OTHER INFORMATION: any nucleotide
<220> FEATURE:
<221> NAME/KEY: misc_feature
<222> LOCATION: (93)..(93)
<223> OTHER INFORMATION: any nucleotide
<220> FEATURE:
<221> NAME/KEY: misc_feature
<222> LOCATION: (105)..(105)
<223> OTHER INFORMATION: any nucleotide
<220> FEATURE:
<221> NAME/KEY: misc_feature
<222> LOCATION: (117)..(117)
<223> OTHER INFORMATION: any nucleotide
<220> FEATURE:
<221> NAME/KEY: misc_feature
<222> LOCATION: (120)..(120)
<223> OTHER INFORMATION: any nucleotide
<220> FEATURE:
<221> NAME/KEY: misc_feature
<222> LOCATION: (123)..(123)
<223> OTHER INFORMATION: any nucleotide
```

-continued

```
<220> FEATURE:
<221> NAME/KEY: misc_feature
<222> LOCATION: (126)..(126)
<223> OTHER INFORMATION: any nucleotide
<220> FEATURE:
<221> NAME/KEY: misc_feature
<222> LOCATION: (132)..(132)
<223> OTHER INFORMATION: any nucleotide
<220> FEATURE:
<221> NAME/KEY: misc_feature
<222> LOCATION: (135)..(135)
<223> OTHER INFORMATION: any nucleotide
<220> FEATURE:
<221> NAME/KEY: misc_feature
<222> LOCATION: (138)..(138)
<223> OTHER INFORMATION: any nucleotide
<220> FEATURE:
<221> NAME/KEY: misc_feature
<222> LOCATION: (147)..(147)
<223> OTHER INFORMATION: any nucleotide
<220> FEATURE:
<221> NAME/KEY: misc_feature
<222> LOCATION: (150)..(150)
<223> OTHER INFORMATION: any nucleotide
<220> FEATURE:
<221> NAME/KEY: misc_feature
<222> LOCATION: (153)..(153)
<223> OTHER INFORMATION: any nucleotide
<220> FEATURE:
<221> NAME/KEY: misc_feature
<222> LOCATION: (165)..(165)
<223> OTHER INFORMATION: any nucleotide
<220> FEATURE:
<221> NAME/KEY: misc_feature
<222> LOCATION: (168)..(168)
<223> OTHER INFORMATION: any nucleotide
<220> FEATURE:
<221> NAME/KEY: misc_feature
<222> LOCATION: (171)..(171)
<223> OTHER INFORMATION: any nucleotide
<220> FEATURE:
<221> NAME/KEY: misc_feature
<222> LOCATION: (183)..(183)
<223> OTHER INFORMATION: any nucleotide
<220> FEATURE:
<221> NAME/KEY: misc_feature
<222> LOCATION: (186)..(186)
<223> OTHER INFORMATION: any nucleotide
<220> FEATURE:
<221> NAME/KEY: misc_feature
<222> LOCATION: (189)..(189)
<223> OTHER INFORMATION: any nucleotide
<220> FEATURE:
<221> NAME/KEY: misc_feature
<222> LOCATION: (192)..(192)
<223> OTHER INFORMATION: any nucleotide
<220> FEATURE:
<221> NAME/KEY: misc_feature
<222> LOCATION: (198)..(198)
<223> OTHER INFORMATION: any nucleotide
<220> FEATURE:
<221> NAME/KEY: misc_feature
<222> LOCATION: (201)..(201)
<223> OTHER INFORMATION: any nucleotide
<220> FEATURE:
<221> NAME/KEY: misc_feature
<222> LOCATION: (207)..(207)
<223> OTHER INFORMATION: any nucleotide
<220> FEATURE:
<221> NAME/KEY: misc_feature
<222> LOCATION: (210)..(210)
<223> OTHER INFORMATION: any nucleotide
<220> FEATURE:
<221> NAME/KEY: misc_feature
<222> LOCATION: (213)..(213)
<223> OTHER INFORMATION: any nucleotide
<220> FEATURE:
<221> NAME/KEY: misc_feature
<222> LOCATION: (231)..(231)
```

```
<223> OTHER INFORMATION: any nucleotide
<220> FEATURE:
<221> NAME/KEY: misc_feature
<222> LOCATION: (237)..(237)
<223> OTHER INFORMATION: any nucleotide

<400> SEQUENCE: 16
wsntayacnw snaaygcnws nggnwsngar gcngcngcna argcntggat hgcnggnmgn      60
garwsnggng gnaaytayaa ygcnacnaay ggncartaya thggnaarta ycarytngcn     120
gcnwsntayy tnggnggnga ytaywsnccn gcnaaycarg armgngtngc ngaycartay     180
gtngcnwsnm gntayggnws ntggacngcn gcncarcart tytggcargc naayggntgg     240 tay                                                                   243

<210> SEQ ID NO 17
<211> LENGTH: 525
<212> TYPE: DNA
<213> ORGANISM: Lactobacillus fermentum
<220> FEATURE:
<221> NAME/KEY: misc_feature
<222> LOCATION: (6)..(6)
<223> OTHER INFORMATION: any nucleotide
<220> FEATURE:
<221> NAME/KEY: misc_feature
<222> LOCATION: (15)..(15)
<223> OTHER INFORMATION: any nucleotide
<220> FEATURE:
<221> NAME/KEY: misc_feature
<222> LOCATION: (18)..(18)
<223> OTHER INFORMATION: any nucleotide
<220> FEATURE:
<221> NAME/KEY: misc_feature
<222> LOCATION: (24)..(24)
<223> OTHER INFORMATION: any nucleotide
<220> FEATURE:
<221> NAME/KEY: misc_feature
<222> LOCATION: (27)..(27)
<223> OTHER INFORMATION: any nucleotide
<220> FEATURE:
<221> NAME/KEY: misc_feature
<222> LOCATION: (33)..(33)
<223> OTHER INFORMATION: any nucleotide
<220> FEATURE:
<221> NAME/KEY: misc_feature
<222> LOCATION: (36)..(36)
<223> OTHER INFORMATION: any nucleotide
<220> FEATURE:
<221> NAME/KEY: misc_feature
<222> LOCATION: (39)..(39)
<223> OTHER INFORMATION: any nucleotide
<220> FEATURE:
<221> NAME/KEY: misc_feature
<222> LOCATION: (42)..(42)
<223> OTHER INFORMATION: any nucleotide
<220> FEATURE:
<221> NAME/KEY: misc_feature
<222> LOCATION: (48)..(48)
<223> OTHER INFORMATION: any nucleotide
<220> FEATURE:
<221> NAME/KEY: misc_feature
<222> LOCATION: (60)..(60)
<223> OTHER INFORMATION: any nucleotide
<220> FEATURE:
<221> NAME/KEY: misc_feature
<222> LOCATION: (72)..(72)
<223> OTHER INFORMATION: any nucleotide
<220> FEATURE:
<221> NAME/KEY: misc_feature
<222> LOCATION: (87)..(87)
<223> OTHER INFORMATION: any nucleotide
<220> FEATURE:
<221> NAME/KEY: misc_feature
<222> LOCATION: (90)..(90)
<223> OTHER INFORMATION: any nucleotide
```

-continued

```
<220> FEATURE:
<221> NAME/KEY: misc_feature
<222> LOCATION: (129)..(129)
<223> OTHER INFORMATION: any nucleotide
<220> FEATURE:
<221> NAME/KEY: misc_feature
<222> LOCATION: (132)..(132)
<223> OTHER INFORMATION: any nucleotide
<220> FEATURE:
<221> NAME/KEY: misc_feature
<222> LOCATION: (141)..(141)
<223> OTHER INFORMATION: any nucleotide
<220> FEATURE:
<221> NAME/KEY: misc_feature
<222> LOCATION: (153)..(153)
<223> OTHER INFORMATION: any nucleotide
<220> FEATURE:
<221> NAME/KEY: misc_feature
<222> LOCATION: (159)..(159)
<223> OTHER INFORMATION: any nucleotide
<220> FEATURE:
<221> NAME/KEY: misc_feature
<222> LOCATION: (180)..(180)
<223> OTHER INFORMATION: any nucleotide
<220> FEATURE:
<221> NAME/KEY: misc_feature
<222> LOCATION: (189)..(189)
<223> OTHER INFORMATION: any nucleotide
<220> FEATURE:
<221> NAME/KEY: misc_feature
<222> LOCATION: (192)..(192)
<223> OTHER INFORMATION: any nucleotide
<220> FEATURE:
<221> NAME/KEY: misc_feature
<222> LOCATION: (198)..(198)
<223> OTHER INFORMATION: any nucleotide
<220> FEATURE:
<221> NAME/KEY: misc_feature
<222> LOCATION: (204)..(204)
<223> OTHER INFORMATION: any nucleotide
<220> FEATURE:
<221> NAME/KEY: misc_feature
<222> LOCATION: (207)..(207)
<223> OTHER INFORMATION: any nucleotide
<220> FEATURE:
<221> NAME/KEY: misc_feature
<222> LOCATION: (219)..(219)
<223> OTHER INFORMATION: any nucleotide
<220> FEATURE:
<221> NAME/KEY: misc_feature
<222> LOCATION: (225)..(225)
<223> OTHER INFORMATION: any nucleotide
<220> FEATURE:
<221> NAME/KEY: misc_feature
<222> LOCATION: (228)..(228)
<223> OTHER INFORMATION: any nucleotide
<220> FEATURE:
<221> NAME/KEY: misc_feature
<222> LOCATION: (240)..(240)
<223> OTHER INFORMATION: any nucleotide
<220> FEATURE:
<221> NAME/KEY: misc_feature
<222> LOCATION: (243)..(243)
<223> OTHER INFORMATION: any nucleotide
<220> FEATURE:
<221> NAME/KEY: misc_feature
<222> LOCATION: (249)..(249)
<223> OTHER INFORMATION: any nucleotide
<220> FEATURE:
<221> NAME/KEY: misc_feature
<222> LOCATION: (255)..(255)
<223> OTHER INFORMATION: any nucleotide
<220> FEATURE:
<221> NAME/KEY: misc_feature
<222> LOCATION: (264)..(264)
<223> OTHER INFORMATION: any nucleotide
<220> FEATURE:
<221> NAME/KEY: misc_feature
<222> LOCATION: (270)..(270)
```

```
<223> OTHER INFORMATION: any nucleotide
<220> FEATURE:
<221> NAME/KEY: misc_feature
<222> LOCATION: (276)..(276)
<223> OTHER INFORMATION: any nucleotide
<220> FEATURE:
<221> NAME/KEY: misc_feature
<222> LOCATION: (285)..(285)
<223> OTHER INFORMATION: any nucleotide
<220> FEATURE:
<221> NAME/KEY: misc_feature
<222> LOCATION: (291)..(291)
<223> OTHER INFORMATION: any nucleotide
<220> FEATURE:
<221> NAME/KEY: misc_feature
<222> LOCATION: (294)..(294)
<223> OTHER INFORMATION: any nucleotide
<220> FEATURE:
<221> NAME/KEY: misc_feature
<222> LOCATION: (300)..(300)
<223> OTHER INFORMATION: any nucleotide
<220> FEATURE:
<221> NAME/KEY: misc_feature
<222> LOCATION: (303)..(303)
<223> OTHER INFORMATION: any nucleotide
<220> FEATURE:
<221> NAME/KEY: misc_feature
<222> LOCATION: (306)..(306)
<223> OTHER INFORMATION: any nucleotide
<220> FEATURE:
<221> NAME/KEY: misc_feature
<222> LOCATION: (309)..(309)
<223> OTHER INFORMATION: any nucleotide
<220> FEATURE:
<221> NAME/KEY: misc_feature
<222> LOCATION: (315)..(315)
<223> OTHER INFORMATION: any nucleotide
<220> FEATURE:
<221> NAME/KEY: misc_feature
<222> LOCATION: (318)..(318)
<223> OTHER INFORMATION: any nucleotide
<220> FEATURE:
<221> NAME/KEY: misc_feature
<222> LOCATION: (321)..(321)
<223> OTHER INFORMATION: any nucleotide
<220> FEATURE:
<221> NAME/KEY: misc_feature
<222> LOCATION: (327)..(327)
<223> OTHER INFORMATION: any nucleotide
<220> FEATURE:
<221> NAME/KEY: misc_feature
<222> LOCATION: (336)..(336)
<223> OTHER INFORMATION: any nucleotide
<220> FEATURE:
<221> NAME/KEY: misc_feature
<222> LOCATION: (339)..(339)
<223> OTHER INFORMATION: any nucleotide
<220> FEATURE:
<221> NAME/KEY: misc_feature
<222> LOCATION: (342)..(342)
<223> OTHER INFORMATION: any nucleotide
<220> FEATURE:
<221> NAME/KEY: misc_feature
<222> LOCATION: (348)..(348)
<223> OTHER INFORMATION: any nucleotide
<220> FEATURE:
<221> NAME/KEY: misc_feature
<222> LOCATION: (351)..(351)
<223> OTHER INFORMATION: any nucleotide
<220> FEATURE:
<221> NAME/KEY: misc_feature
<222> LOCATION: (354)..(354)
<223> OTHER INFORMATION: any nucleotide
<220> FEATURE:
<221> NAME/KEY: misc_feature
<222> LOCATION: (366)..(366)
<223> OTHER INFORMATION: any nucleotide
<220> FEATURE:
<221> NAME/KEY: misc_feature
```

```
<222> LOCATION: (369)..(369)
<223> OTHER INFORMATION: any nucleotide
<220> FEATURE:
<221> NAME/KEY: misc_feature
<222> LOCATION: (375)..(375)
<223> OTHER INFORMATION: any nucleotide
<220> FEATURE:
<221> NAME/KEY: misc_feature
<222> LOCATION: (387)..(387)
<223> OTHER INFORMATION: any nucleotide
<220> FEATURE:
<221> NAME/KEY: misc_feature
<222> LOCATION: (399)..(399)
<223> OTHER INFORMATION: any nucleotide
<220> FEATURE:
<221> NAME/KEY: misc_feature
<222> LOCATION: (402)..(402)
<223> OTHER INFORMATION: any nucleotide
<220> FEATURE:
<221> NAME/KEY: misc_feature
<222> LOCATION: (405)..(405)
<223> OTHER INFORMATION: any nucleotide
<220> FEATURE:
<221> NAME/KEY: misc_feature
<222> LOCATION: (408)..(408)
<223> OTHER INFORMATION: any nucleotide
<220> FEATURE:
<221> NAME/KEY: misc_feature
<222> LOCATION: (414)..(414)
<223> OTHER INFORMATION: any nucleotide
<220> FEATURE:
<221> NAME/KEY: misc_feature
<222> LOCATION: (417)..(417)
<223> OTHER INFORMATION: any nucleotide
<220> FEATURE:
<221> NAME/KEY: misc_feature
<222> LOCATION: (420)..(420)
<223> OTHER INFORMATION: any nucleotide
<220> FEATURE:
<221> NAME/KEY: misc_feature
<222> LOCATION: (429)..(429)
<223> OTHER INFORMATION: any nucleotide
<220> FEATURE:
<221> NAME/KEY: misc_feature
<222> LOCATION: (432)..(432)
<223> OTHER INFORMATION: any nucleotide
<220> FEATURE:
<221> NAME/KEY: misc_feature
<222> LOCATION: (435)..(435)
<223> OTHER INFORMATION: any nucleotide
<220> FEATURE:
<221> NAME/KEY: misc_feature
<222> LOCATION: (447)..(447)
<223> OTHER INFORMATION: any nucleotide
<220> FEATURE:
<221> NAME/KEY: misc_feature
<222> LOCATION: (450)..(450)
<223> OTHER INFORMATION: any nucleotide
<220> FEATURE:
<221> NAME/KEY: misc_feature
<222> LOCATION: (453)..(453)
<223> OTHER INFORMATION: any nucleotide
<220> FEATURE:
<221> NAME/KEY: misc_feature
<222> LOCATION: (465)..(465)
<223> OTHER INFORMATION: any nucleotide
<220> FEATURE:
<221> NAME/KEY: misc_feature
<222> LOCATION: (468)..(468)
<223> OTHER INFORMATION: any nucleotide
<220> FEATURE:
<221> NAME/KEY: misc_feature
<222> LOCATION: (471)..(471)
<223> OTHER INFORMATION: any nucleotide
<220> FEATURE:
<221> NAME/KEY: misc_feature
<222> LOCATION: (474)..(474)
<223> OTHER INFORMATION: any nucleotide
<220> FEATURE:
```

-continued

<221> NAME/KEY: misc_feature
<222> LOCATION: (480)..(480)
<223> OTHER INFORMATION: any nucleotide
<220> FEATURE:
<221> NAME/KEY: misc_feature
<222> LOCATION: (483)..(483)
<223> OTHER INFORMATION: any nucleotide
<220> FEATURE:
<221> NAME/KEY: misc_feature
<222> LOCATION: (489)..(489)
<223> OTHER INFORMATION: any nucleotide
<220> FEATURE:
<221> NAME/KEY: misc_feature
<222> LOCATION: (492)..(492)
<223> OTHER INFORMATION: any nucleotide
<220> FEATURE:
<221> NAME/KEY: misc_feature
<222> LOCATION: (495)..(495)
<223> OTHER INFORMATION: any nucleotide
<220> FEATURE:
<221> NAME/KEY: misc_feature
<222> LOCATION: (513)..(513)
<223> OTHER INFORMATION: any nucleotide
<220> FEATURE:
<221> NAME/KEY: misc_feature
<222> LOCATION: (519)..(519)
<223> OTHER INFORMATION: any nucleotide

<400> SEQUENCE: 17
gayacnatht ayacngtnca rwsnggngay acnytnwsng gnathwsnta yaarttygcn 60
aargayaayw snatgathaa ygayytngcn aaraaraaya ayathcarga yathaayaar 120
athttygtng gncaraaryt nathathaar wsngayggng arathcarga rtayaaygcn 180
caraaygcng cnaaygcnaa ygtngcnaay aayaayacnc argcnacnca rcarcaracn 240
gcncargcnc arccncarca rgcncarwsn cargcnaayc arwsntayac nwsnaaygcn 300
wsnggnwsng argcngcngc naargcntgg athgcnggnm gngarwsngg nggnaaytay 360
aaygcnacna ayggncarta yathggnaar taycarytng cngcnwsnta yytnggnggn 420
gaytaywsnc cngcnaayca rgarmgngtn gcngaycart aygtngcnws nmgntayggn 480
wsntggacng cngcncarca rttytggcar gcnaayggnt ggtay 525

<210> SEQ ID NO 18
<211> LENGTH: 615
<212> TYPE: DNA
<213> ORGANISM: Lactobacillus fermentum
<220> FEATURE:
<221> NAME/KEY: misc_feature
<222> LOCATION: (9)..(9)
<223> OTHER INFORMATION: any nucleotide
<220> FEATURE:
<221> NAME/KEY: misc_feature
<222> LOCATION: (24)..(24)
<223> OTHER INFORMATION: any nucleotide
<220> FEATURE:
<221> NAME/KEY: misc_feature
<222> LOCATION: (30)..(30)
<223> OTHER INFORMATION: any nucleotide
<220> FEATURE:
<221> NAME/KEY: misc_feature
<222> LOCATION: (33)..(33)
<223> OTHER INFORMATION: any nucleotide
<220> FEATURE:
<221> NAME/KEY: misc_feature
<222> LOCATION: (36)..(36)
<223> OTHER INFORMATION: any nucleotide
<220> FEATURE:
<221> NAME/KEY: misc_feature
<222> LOCATION: (39)..(39)
<223> OTHER INFORMATION: any nucleotide
<220> FEATURE:
<221> NAME/KEY: misc_feature

```
<222> LOCATION: (42)..(42)
<223> OTHER INFORMATION: any nucleotide
<220> FEATURE:
<221> NAME/KEY: misc_feature
<222> LOCATION: (45)..(45)
<223> OTHER INFORMATION: any nucleotide
<220> FEATURE:
<221> NAME/KEY: misc_feature
<222> LOCATION: (48)..(48)
<223> OTHER INFORMATION: any nucleotide
<220> FEATURE:
<221> NAME/KEY: misc_feature
<222> LOCATION: (51)..(51)
<223> OTHER INFORMATION: any nucleotide
<220> FEATURE:
<221> NAME/KEY: misc_feature
<222> LOCATION: (54)..(54)
<223> OTHER INFORMATION: any nucleotide
<220> FEATURE:
<221> NAME/KEY: misc_feature
<222> LOCATION: (57)..(57)
<223> OTHER INFORMATION: any nucleotide
<220> FEATURE:
<221> NAME/KEY: misc_feature
<222> LOCATION: (60)..(60)
<223> OTHER INFORMATION: any nucleotide
<220> FEATURE:
<221> NAME/KEY: misc_feature
<222> LOCATION: (63)..(63)
<223> OTHER INFORMATION: any nucleotide
<220> FEATURE:
<221> NAME/KEY: misc_feature
<222> LOCATION: (66)..(66)
<223> OTHER INFORMATION: any nucleotide
<220> FEATURE:
<221> NAME/KEY: misc_feature
<222> LOCATION: (69)..(69)
<223> OTHER INFORMATION: any nucleotide
<220> FEATURE:
<221> NAME/KEY: misc_feature
<222> LOCATION: (72)..(72)
<223> OTHER INFORMATION: any nucleotide
<220> FEATURE:
<221> NAME/KEY: misc_feature
<222> LOCATION: (75)..(75)
<223> OTHER INFORMATION: any nucleotide
<220> FEATURE:
<221> NAME/KEY: misc_feature
<222> LOCATION: (78)..(78)
<223> OTHER INFORMATION: any nucleotide
<220> FEATURE:
<221> NAME/KEY: misc_feature
<222> LOCATION: (81)..(81)
<223> OTHER INFORMATION: any nucleotide
<220> FEATURE:
<221> NAME/KEY: misc_feature
<222> LOCATION: (84)..(84)
<223> OTHER INFORMATION: any nucleotide
<220> FEATURE:
<221> NAME/KEY: misc_feature
<222> LOCATION: (90)..(90)
<223> OTHER INFORMATION: any nucleotide
<220> FEATURE:
<221> NAME/KEY: misc_feature
<222> LOCATION: (96)..(96)
<223> OTHER INFORMATION: any nucleotide
<220> FEATURE:
<221> NAME/KEY: misc_feature
<222> LOCATION: (105)..(105)
<223> OTHER INFORMATION: any nucleotide
<220> FEATURE:
<221> NAME/KEY: misc_feature
<222> LOCATION: (108)..(108)
<223> OTHER INFORMATION: any nucleotide
<220> FEATURE:
<221> NAME/KEY: misc_feature
<222> LOCATION: (114)..(114)
<223> OTHER INFORMATION: any nucleotide
<220> FEATURE:
```

-continued

```
<221> NAME/KEY: misc_feature
<222> LOCATION: (117)..(117)
<223> OTHER INFORMATION: any nucleotide
<220> FEATURE:
<221> NAME/KEY: misc_feature
<222> LOCATION: (123)..(123)
<223> OTHER INFORMATION: any nucleotide
<220> FEATURE:
<221> NAME/KEY: misc_feature
<222> LOCATION: (126)..(126)
<223> OTHER INFORMATION: any nucleotide
<220> FEATURE:
<221> NAME/KEY: misc_feature
<222> LOCATION: (129)..(129)
<223> OTHER INFORMATION: any nucleotide
<220> FEATURE:
<221> NAME/KEY: misc_feature
<222> LOCATION: (132)..(132)
<223> OTHER INFORMATION: any nucleotide
<220> FEATURE:
<221> NAME/KEY: misc_feature
<222> LOCATION: (138)..(138)
<223> OTHER INFORMATION: any nucleotide
<220> FEATURE:
<221> NAME/KEY: misc_feature
<222> LOCATION: (150)..(150)
<223> OTHER INFORMATION: any nucleotide
<220> FEATURE:
<221> NAME/KEY: misc_feature
<222> LOCATION: (162)..(162)
<223> OTHER INFORMATION: any nucleotide
<220> FEATURE:
<221> NAME/KEY: misc_feature
<222> LOCATION: (177)..(177)
<223> OTHER INFORMATION: any nucleotide
<220> FEATURE:
<221> NAME/KEY: misc_feature
<222> LOCATION: (180)..(180)
<223> OTHER INFORMATION: any nucleotide
<220> FEATURE:
<221> NAME/KEY: misc_feature
<222> LOCATION: (219)..(219)
<223> OTHER INFORMATION: any nucleotide
<220> FEATURE:
<221> NAME/KEY: misc_feature
<222> LOCATION: (222)..(222)
<223> OTHER INFORMATION: any nucleotide
<220> FEATURE:
<221> NAME/KEY: misc_feature
<222> LOCATION: (231)..(231)
<223> OTHER INFORMATION: any nucleotide
<220> FEATURE:
<221> NAME/KEY: misc_feature
<222> LOCATION: (243)..(243)
<223> OTHER INFORMATION: any nucleotide
<220> FEATURE:
<221> NAME/KEY: misc_feature
<222> LOCATION: (249)..(249)
<223> OTHER INFORMATION: any nucleotide
<220> FEATURE:
<221> NAME/KEY: misc_feature
<222> LOCATION: (270)..(270)
<223> OTHER INFORMATION: any nucleotide
<220> FEATURE:
<221> NAME/KEY: misc_feature
<222> LOCATION: (279)..(279)
<223> OTHER INFORMATION: any nucleotide
<220> FEATURE:
<221> NAME/KEY: misc_feature
<222> LOCATION: (282)..(282)
<223> OTHER INFORMATION: any nucleotide
<220> FEATURE:
<221> NAME/KEY: misc_feature
<222> LOCATION: (288)..(288)
<223> OTHER INFORMATION: any nucleotide
<220> FEATURE:
<221> NAME/KEY: misc_feature
<222> LOCATION: (294)..(294)
<223> OTHER INFORMATION: any nucleotide
```

```
<220> FEATURE:
<221> NAME/KEY: misc_feature
<222> LOCATION: (297)..(297)
<223> OTHER INFORMATION: any nucleotide
<220> FEATURE:
<221> NAME/KEY: misc_feature
<222> LOCATION: (309)..(309)
<223> OTHER INFORMATION: any nucleotide
<220> FEATURE:
<221> NAME/KEY: misc_feature
<222> LOCATION: (315)..(315)
<223> OTHER INFORMATION: any nucleotide
<220> FEATURE:
<221> NAME/KEY: misc_feature
<222> LOCATION: (318)..(318)
<223> OTHER INFORMATION: any nucleotide
<220> FEATURE:
<221> NAME/KEY: misc_feature
<222> LOCATION: (330)..(330)
<223> OTHER INFORMATION: any nucleotide
<220> FEATURE:
<221> NAME/KEY: misc_feature
<222> LOCATION: (333)..(333)
<223> OTHER INFORMATION: any nucleotide
<220> FEATURE:
<221> NAME/KEY: misc_feature
<222> LOCATION: (339)..(339)
<223> OTHER INFORMATION: any nucleotide
<220> FEATURE:
<221> NAME/KEY: misc_feature
<222> LOCATION: (345)..(345)
<223> OTHER INFORMATION: any nucleotide
<220> FEATURE:
<221> NAME/KEY: misc_feature
<222> LOCATION: (354)..(354)
<223> OTHER INFORMATION: any nucleotide
<220> FEATURE:
<221> NAME/KEY: misc_feature
<222> LOCATION: (360)..(360)
<223> OTHER INFORMATION: any nucleotide
<220> FEATURE:
<221> NAME/KEY: misc_feature
<222> LOCATION: (366)..(366)
<223> OTHER INFORMATION: any nucleotide
<220> FEATURE:
<221> NAME/KEY: misc_feature
<222> LOCATION: (375)..(375)
<223> OTHER INFORMATION: any nucleotide
<220> FEATURE:
<221> NAME/KEY: misc_feature
<222> LOCATION: (381)..(381)
<223> OTHER INFORMATION: any nucleotide
<220> FEATURE:
<221> NAME/KEY: misc_feature
<222> LOCATION: (384)..(384)
<223> OTHER INFORMATION: any nucleotide
<220> FEATURE:
<221> NAME/KEY: misc_feature
<222> LOCATION: (390)..(390)
<223> OTHER INFORMATION: any nucleotide
<220> FEATURE:
<221> NAME/KEY: misc_feature
<222> LOCATION: (393)..(393)
<223> OTHER INFORMATION: any nucleotide
<220> FEATURE:
<221> NAME/KEY: misc_feature
<222> LOCATION: (396)..(396)
<223> OTHER INFORMATION: any nucleotide
<220> FEATURE:
<221> NAME/KEY: misc_feature
<222> LOCATION: (399)..(399)
<223> OTHER INFORMATION: any nucleotide
<220> FEATURE:
<221> NAME/KEY: misc_feature
<222> LOCATION: (405)..(405)
<223> OTHER INFORMATION: any nucleotide
<220> FEATURE:
<221> NAME/KEY: misc_feature
<222> LOCATION: (408)..(408)
```

```
<223> OTHER INFORMATION: any nucleotide
<220> FEATURE:
<221> NAME/KEY: misc_feature
<222> LOCATION: (411)..(411)
<223> OTHER INFORMATION: any nucleotide
<220> FEATURE:
<221> NAME/KEY: misc_feature
<222> LOCATION: (417)..(417)
<223> OTHER INFORMATION: any nucleotide
<220> FEATURE:
<221> NAME/KEY: misc_feature
<222> LOCATION: (426)..(426)
<223> OTHER INFORMATION: any nucleotide
<220> FEATURE:
<221> NAME/KEY: misc_feature
<222> LOCATION: (429)..(429)
<223> OTHER INFORMATION: any nucleotide
<220> FEATURE:
<221> NAME/KEY: misc_feature
<222> LOCATION: (432)..(432)
<223> OTHER INFORMATION: any nucleotide
<220> FEATURE:
<221> NAME/KEY: misc_feature
<222> LOCATION: (438)..(438)
<223> OTHER INFORMATION: any nucleotide
<220> FEATURE:
<221> NAME/KEY: misc_feature
<222> LOCATION: (441)..(441)
<223> OTHER INFORMATION: any nucleotide
<220> FEATURE:
<221> NAME/KEY: misc_feature
<222> LOCATION: (444)..(444)
<223> OTHER INFORMATION: any nucleotide
<220> FEATURE:
<221> NAME/KEY: misc_feature
<222> LOCATION: (456)..(456)
<223> OTHER INFORMATION: any nucleotide
<220> FEATURE:
<221> NAME/KEY: misc_feature
<222> LOCATION: (459)..(459)
<223> OTHER INFORMATION: any nucleotide
<220> FEATURE:
<221> NAME/KEY: misc_feature
<222> LOCATION: (465)..(465)
<223> OTHER INFORMATION: any nucleotide
<220> FEATURE:
<221> NAME/KEY: misc_feature
<222> LOCATION: (477)..(477)
<223> OTHER INFORMATION: any nucleotide
<220> FEATURE:
<221> NAME/KEY: misc_feature
<222> LOCATION: (489)..(489)
<223> OTHER INFORMATION: any nucleotide
<220> FEATURE:
<221> NAME/KEY: misc_feature
<222> LOCATION: (492)..(492)
<223> OTHER INFORMATION: any nucleotide
<220> FEATURE:
<221> NAME/KEY: misc_feature
<222> LOCATION: (495)..(495)
<223> OTHER INFORMATION: any nucleotide
<220> FEATURE:
<221> NAME/KEY: misc_feature
<222> LOCATION: (498)..(498)
<223> OTHER INFORMATION: any nucleotide
<220> FEATURE:
<221> NAME/KEY: misc_feature
<222> LOCATION: (504)..(504)
<223> OTHER INFORMATION: any nucleotide
<220> FEATURE:
<221> NAME/KEY: misc_feature
<222> LOCATION: (507)..(507)
<223> OTHER INFORMATION: any nucleotide
<220> FEATURE:
<221> NAME/KEY: misc_feature
<222> LOCATION: (510)..(510)
<223> OTHER INFORMATION: any nucleotide
<220> FEATURE:
<221> NAME/KEY: misc_feature
```

-continued

<222> LOCATION: (519)..(519)
<223> OTHER INFORMATION: any nucleotide
<220> FEATURE:
<221> NAME/KEY: misc_feature
<222> LOCATION: (522)..(522)
<223> OTHER INFORMATION: any nucleotide
<220> FEATURE:
<221> NAME/KEY: misc_feature
<222> LOCATION: (525)..(525)
<223> OTHER INFORMATION: any nucleotide
<220> FEATURE:
<221> NAME/KEY: misc_feature
<222> LOCATION: (537)..(537)
<223> OTHER INFORMATION: any nucleotide
<220> FEATURE:
<221> NAME/KEY: misc_feature
<222> LOCATION: (540)..(540)
<223> OTHER INFORMATION: any nucleotide
<220> FEATURE:
<221> NAME/KEY: misc_feature
<222> LOCATION: (543)..(543)
<223> OTHER INFORMATION: any nucleotide
<220> FEATURE:
<221> NAME/KEY: misc_feature
<222> LOCATION: (555)..(555)
<223> OTHER INFORMATION: any nucleotide
<220> FEATURE:
<221> NAME/KEY: misc_feature
<222> LOCATION: (558)..(558)
<223> OTHER INFORMATION: any nucleotide
<220> FEATURE:
<221> NAME/KEY: misc_feature
<222> LOCATION: (561)..(561)
<223> OTHER INFORMATION: any nucleotide
<220> FEATURE:
<221> NAME/KEY: misc_feature
<222> LOCATION: (564)..(564)
<223> OTHER INFORMATION: any nucleotide
<220> FEATURE:
<221> NAME/KEY: misc_feature
<222> LOCATION: (570)..(570)
<223> OTHER INFORMATION: any nucleotide
<220> FEATURE:
<221> NAME/KEY: misc_feature
<222> LOCATION: (573)..(573)
<223> OTHER INFORMATION: any nucleotide
<220> FEATURE:
<221> NAME/KEY: misc_feature
<222> LOCATION: (579)..(579)
<223> OTHER INFORMATION: any nucleotide
<220> FEATURE:
<221> NAME/KEY: misc_feature
<222> LOCATION: (582)..(582)
<223> OTHER INFORMATION: any nucleotide
<220> FEATURE:
<221> NAME/KEY: misc_feature
<222> LOCATION: (585)..(585)
<223> OTHER INFORMATION: any nucleotide
<220> FEATURE:
<221> NAME/KEY: misc_feature
<222> LOCATION: (603)..(603)
<223> OTHER INFORMATION: any nucleotide
<220> FEATURE:
<221> NAME/KEY: misc_feature
<222> LOCATION: (609)..(609)
<223> OTHER INFORMATION: any nucleotide

<400> SEQUENCE: 18
atgathwsna araaraaytt ygcnaargtn wsngcnacny tnggngcngt ngcnytnggn 60
gtnwsngcna cngcnacngc ngcnaaygcn gayacnatht ayacngtnca rwsnggngay 120
acnytnwsng gnathwsnta yaarttygcn aargayaayw snatgathaa ygayytngcn 180
aaraaraaya ayathcarga yathaayaar athttygtng gncaraaryt nathathaar 240
wsngayggng arathcarga rtayaaygcn caraaygcng cnaaygcnaa ygtngcnaay 300

-continued

```
aayaayacnc argcnacnca rcarcaracn gcncargcnc arccncarca rgcncarwsn      360
cargcnaayc arwsntayac nwsnaaygcn wsnggnwsng argcngcngc naargcntgg      420
athgcnggnm gngarwsngg nggnaaytay aaygcnacna ayggncarta yathggnaar      480
taycarytng cngcnwsnta yytnggnggn gaytaywsnc cngcnaayca rgarmgngtn      540
gcngaycart aygtngcnws nmgntayggn wsntggacng cngcncarca rttytggcar      600
gcnaayggnt ggtay                                                      615

<210> SEQ ID NO 19
<211> LENGTH: 310
<212> TYPE: DNA
<213> ORGANISM: Lactobacillus fermentum

<400> SEQUENCE: 19
taaagatagt tataaacgga aaataaaggg cggttttgga gcaaatatga aattttgcg       60 aagaaatcag cttttttat ttattttttt ataaatcatc tgtaaaagtt atgcaaaccg      120
aaaacgcaac ccgcacaagg aattagccga ttatgactat aatattttaa aagctatatt    180
acaaaaagca aacggagagt agtaaataga aatggtgctg ttacagcttt gtaatattaa    240
gagtgtagta tagggtgt tgaaacggaa aagataattt gctaaataat aaaggatggt      300
tatttaattt                                                           310

<210> SEQ ID NO 20
<211> LENGTH: 150
<212> TYPE: DNA
<213> ORGANISM: Lactobacillus fermentum

<400> SEQUENCE: 20
aataaataag attaatcaat tttattgcga gactgatgga atattattc cttctgtctc       60 gcttttttgg gctaatatgt tataatggta gtacttctta tggggatgtt tatggattcg     120
acaggtatag gtcgagtttc aactgcgttt                                      150
```

PROTEIN EXPRESSION

FIELD OF THE INVENTION

The invention relates to a peptide and a nucleic acid molecule and to uses thereof for producing heterologous proteins, pro-biotic organisms and functional food components and products.

BACKGROUND OF THE INVENTION

Lactic acid bacteria, such as *Lactobacillus* and *Lactococcus*, and other Gram-positive bacteria such as *Bifidobacterium, Leuconostoc* and *Streptococcus*, are widely used for manufacturing food products and for the fermentation of raw agricultural products.

As these bacteria tend to be harmless and tend to remain viable in the intestinal environment, there is now interest in using these bacteria to produce heterogenous proteins (i.e. proteins that are not naturally produced by the bacteria), especially for use in manufacturing functional food products that provide beneficial health effects, and also in the manufacture of new bio-pharmaceutical products.

In view of these potential applications of lactic acid bacteria, there is a need for molecules that can be expressed on the cell surface of Gram-positive bacteria such as *Lactobacillus, Lactococcus, Bifidobacterium, Leuconostoc* and *Streptococcus*, or for example, in a culture supernatant derived from these bacteria. Further, there is a need for molecules that can be expressed in lactic acid bacteria together with a heterogenous protein in the form of a fusion protein.

SUMMARY OF THE INVENTION

The invention provides a peptide having at least about 75% amino acid homology with the sequence shown in SEQ ID No: 2. The peptide of the invention also can include an amino acid homology with the sequence shown in SEQ ID No: 2 corresponding to at least about 80%, at least about 85%, at least about 90% or can include the amino acid sequence shown in SEQ ID No: 2. The peptide of the invention can further include an amino acid sequence selected from the sequences shown in SEQ ID Nos: 1, 3 or 4-6.

DESCRIPTION OF THE INVENTION

The invention seeks to address the above described need and accordingly, in one aspect, the invention provides a peptide including a LysM domain at the N-terminus of the peptide, an apf-like domain at the C-terminus of the peptide and a glutamine rich region that is arranged between the LysM and apf-like domains.

As described herein, the inventors have isolated and characterised a novel bacterial peptide that is expressed on the cell surface of *Lactobacillus fermentum*. The peptide is also secreted from the cell surface and has a high relative abundance in culture supernatant, suggesting that it is relatively stable when secreted into solution. This protein has been named "Small Exported Protein" or "Sep".

In view of the stable expression of Sep on the cell surface and in culture supernatant, the inventors recognised that Sep would be particularly useful for targeting expression of heterologous proteins to the cell surface of bacteria that are preferred for use in the preparation of functional food components, especially components produced from Gram-positive bacteria such as *Lactobacillus, Lactococcus, Bifidobacterium, Leuconostoc* and *Streptococcus*.

LysM domains, otherwise known as a "lysin motif domains" have been observed in enzymes capable of binding to proteoglycan such as transglycosylases derived from *E. coli*. An example of a LsyM domain is that found in lytic murein transglycosylase D (MltD) of *E. coli* (Bateman, A., and M. Bycroft. 2000. The structure of a LysM domain from *E. coli* membrane-bound lytic murein transglycosylase D (MltD). J. Mol. Biol. 299:1113-1119).

The LysM domain of the peptide of the invention is typically about 40 to 50 amino acids in length, although it may have fewer or more residues. Typically, the LysM domain has a sequence shown in SEQ ID No: 1.

Apf-like domains, otherwise known as "aggregation-promoting factor domains" are understood to have a role in the attachment of proteins to the bacterial cell wall. Examples of apf domains include those found in the apf1 and apf2 proteins of *L. johnsonni* and *L. gasseri* (Ventura, M., I. Jankovic, D. C. Walker, R. D. Pridmore, and R. Zink. 2002. Identification and characterization of novel surface proteins in *Lactobacillus johnsonii* and *Lactobacillus gasseri*. Appl. Environ. Microbiol. 68:6172-6181).

The apf domain of the peptide of the invention is typically about 80 amino acids in length, although it may have fewer or more residues. Typically, the apf domain has a sequence shown in SEQ ID No:2.

The glutamine rich region of the peptide of the invention typically has about 13 glutamine residues in a sequence having about 44 residues. This region is typically hydrophilic. Typically the glutamine rich region has a sequence shown in SEQ ID No:3.

The peptide of the invention may further include a secretion signal sequence, otherwise known as a "leader sequence". The secretion signal sequence has a role in the secretion of the peptide through the cell membranes, so that the peptide may be attached to the cell surface and/or secreted from the cell surface, for example, into a liquid culture. Typically the secretion signal sequence has about 30 amino acids in length, although it may have fewer or more residues. Typically, the secretion signal sequence has a sequence shown in SEQ ID No: 4.

Typically the peptide of the invention has the sequence shown in SEQ ID NO: 5. Where the peptide further includes a secretion signal sequence, the peptide typically has the sequence shown in SEQ ID No:6.

The inventors recognise that the secretion signal sequence, LysM domain, glutamine rich region and apf domain each have utility as separate functional units, for example in the expression of heterologous proteins. Examples of these utilities are described further below.

For example, the secretion signal sequence is particularly useful for targeting the expression of a heterologous protein to the cell surface of Gram-positive bacteria such as *Lactobacillus, Lactococcus, Bifidobacterium, Leuconostoc* and *Streptococcus* Accordingly, the secretion signal sequence is particularly useful for producing, for example, functional food components that contain a heterologous protein of interest, and in particular, a protein that is not naturally expressed by these bacteria.

Thus in one aspect, the invention provides a peptide including the sequence shown in SEQ ID No: 6.

As LysM domains have been shown to bind to proteoglycan, it is recognised that the LysM domain may be particularly useful for binding bioactive compounds that include carbohydrate, for example, for the purpose of concentrating bioactive compounds at a site of interest, such as intestinal mucosal epithelium. Alternatively, the LysM domain may be particularly useful for removing bioactives that include carbohydrate, such as pathogenic bacteria, from a site of interest, such as intestinal mucosal epithelium.

Thus in one aspect, the invention provides a peptide including the sequence shown in SEQ ID No: 1.

As apf domains are understood to have a role in the attachment of some S-layer proteins to the bacterial cell wall, the apf domain may be particularly useful for attaching a heterologous protein to the cell surface of Gram-positive bacteria such as *Lactobacillus, Lactococcus, Bifidobacterium, Leuconostoc* and *Streptococcus* Accordingly, the apf domain may be useful for producing, for example, functional food components that contain a protein of interest.

Thus in one aspect, the invention provides a peptide including the sequence shown in SEQ ID No: 2.

As the inventors have found that the glutamine rich region of the peptide is particularly hydrophilic, they recognise that this region may be very useful in a chimeric protein or fusion protein (described further herein) for spacing hydrophobic domains of a fusion protein apart, thus improving the functionality of each hydrophobic domain. Thus the inventors envisage that the glutamine rich region will have particular utility in the expression of heterologous proteins by Gram-positive bacteria such as *Lactobacillus, Lactococcus, Bifidobacterium, Leuconostoc* and *Streptococcus*.

Thus in one aspect, the invention provides a peptide including the sequence shown in SEQ ID No: 3.

It will be understood that the peptide of the invention may include one or more of the sequences shown in SEQ ID No:1, 2, 3 and 4.

The peptide of the invention is typically about 175 amino acid residues in length, although it may include more amino acid residues. When the peptide is attached to the secretion signal sequence, it is typically about 205 amino acid residues in length.

The inventors recognise that a peptide that includes a sequence that, but for one or more amino acid residues, is essentially the same as the sequence shown in SEQ ID No: 5, would be expected to have a capacity to be expressed either on the surface of Gram-positive bacteria such as *Lactobacillus, Lactococcus, Bifidobacterium, Leuconostoc* and *Streptococcus*, or in a culture supernatant derived therefrom. These peptides could be made according to the processes described further herein. The capacity of these peptides to be expressed on the cell surface or secreted from the cell surface, for example, into a culture supernatant, could be determined by the assays described further herein.

In view of the above, it will be understood that the invention includes peptides that have an amino acid sequence that is homologous to the sequence shown in one of SEQ ID Nos: 1, 2, 3, 4, 5 and 6. These peptides are referred to as "variants". Further to amino acid sequence homology with one of the sequences of SEQ ID Nos: 1, 2, 3, 4, 5 and 6, the variants are characterised in terms of a capacity to be expressed either on the surface of Gram-positive bacteria such as *Lactobacillus, Lactococcus, Bifidobacterium, Leuconostoc* and *Streptococcus*, or in a culture supernatant derived therefrom, as determined by the assays described herein.

"Homology" with respect to amino acid sequence is defined as the percentage of amino acid residues in a candidate sequence that are identical with the amino acid residues of one of the sequences of SEQ ID Nos 1, 2, 3, 4, 5 and 6, after aligning the sequences and introducing gaps if necessary to achieve the maximum identity. No N- or C-terminal extension or deletion in the candidate sequence shall be construed as reducing homology. An example of an algorithm for aligning sequences is CLUSTAL W.

Typically a variant is a peptide that has for example, at least about 75% amino acid homology with one of the sequences of SEQ ID Nos 1, 2, 3, 4, 5 and 6. The variant may have at least 80%, more typically, greater than 85% sequence homology, for example, 90% amino acid homology, with one of the sequences of SEQ ID Nos 1, 2, 3, 4, 5 and 6. However, a variant may exhibit less than 50% sequence homology with the sequence of SEQ ID Nos 1, 2, 3, 4, 5 and 6 and still retain the characteristics of a variant as described herein.

As described herein, peptides of the invention, including variants, may be prepared by chemical synthesis methodologies or by recombinant DNA technology. For example, peptides of the invention can be prepared from monomers using a chemical synthesis methodology based on the sequential addition of amino acid residues, for example as described in Merrifield, J. *Am. Chem. Soc.*, 85: 2149 (1963). These monomers may be naturally occurring residues, or non naturally occurring residues, examples of which are described below. Alternatively, the peptides of the invention, and in particular, a variant, can be prepared enzymatically or chemically by treating a peptide including the sequence shown in one of SEQ ID Nos: 1, 2, 3, 4, 5 or 6. Where the peptides are to be synthesised by recombinant DNA technology, they may be prepared by random or predetermined mutation (eg site directed PCR mutagenesis) of a nucleic acid molecule that encodes an amino acid sequence shown in one of SEQ ID Nos: 1, 2, 3, 4, 5 or 6, or a sequence that has homology with one of the sequences of SEQ ID Nos: 1, 2, 3, 4, 5 and 6, and expression of the sequence in a host cell to obtain the peptide. This is a particularly useful process for preparing variants. An alternative process is de novo chemical synthesis of a nucleic acid molecule that encodes one of the sequences of SEQ ID Nos: 1, 2, 3, 4, 5 and 6 or a sequence that is homologous to one of the sequences of SEQ ID Nos: 1, 2, 3, 4, 5 and 6 and expression of the sequence in the host cell to obtain the peptide.

The peptides of the invention that are variants of one of the sequences of SEQ ID Nos: 1, 2, 3, 4, 5 and 6, typically differ in terms of one or more conservative amino acid substitutions from these sequences. Examples of conservative substitutions are shown in Table 1 below.

TABLE 1

| Original Residue | Exemplary Conservative Substitution | Preferred Conservative Substitution |
| --- | --- | --- |
| Ala | Val, Leu, Ile | Val |
| Arg | Lys, Gln, Asn | Lys |
| Asn | Gln Lys His Phe | Gln |
| Asp | Glu | Glu |
| Cys | Ser | Ser |
| Gln | Asn | Asn |
| Glu | Asp | Asp |
| Gly | Pro | Pro |
| His | Asn, Gln, Lys, Arg | Arg |
| Ile | Leu, Val, Met, Ala, Phe | Leu |
| Leu | Ile, Val, Met, Ala, Phe | Ile |
| Lys | Arg, Gln, Asn | Arg |
| Met | Leu, Phe, Ile | Leu |
| Phe | Lue, Val, Ile, Ala | Leu |
| Pro | Gly | Gly |
| Ser | Thr | Thr |
| Thr | Ser | Ser |
| Trp | Tyr | Tyr |
| Thr | Trp, Phe, Thr, Ser | Phe |
| Val | Ile, Leu, Met, Phe, Ala | Leu |

As noted above, the peptides of the invention may include non naturally occurring amino acid residues. Commonly encountered amino acids which are not encoded by the genetic code, include:

2-amino adipic acid (Aad) for Glu and Asp;
2-aminopimelic acid (Apm) for Glu and Asp;
2-aminobutyric (Abu) acid for Met, Leu, and other aliphatic amino acids;
2-aminoheptanoic acid (Ahe) for Met, Leu and other aliphatic amino acids;
2-aminoisobutyric acid (Aib) for Gly;
cyclohexylalanine (Cha) for Val, and Leu and Ile;
homoarginine (Har) for Arg and Lys;
2,3-diaminopropionic acid (Dpr) for Lys, Arg and His;
N-ethylglycine (EtGly) for Gly, Pro, and Ala;
N-ethylasparigine (EtAsn) for Asn, and Gln;
Hydroxyllysine (Hyl) for Lys;
allohydroxyllysine (AHyl) for Lys;
3-(and 4) hydroxyproline (3Hyp, 4Hyp) for Pro, Ser, and Thr;
alloisoleucine (Alle) for Ile, Leu, and Val;
p-amidinophenylalanine for Ala;
N-methylglycine (MeGly, sarcosine) for Gly, Pro, Ala.
N-methylisoleucine (MeIle) for Ile;
Norvaline (Nva) for Met and other aliphatic amino acids;
Norleucine (Nle) for Met and other aliphatic amino acids;
Ornithine (Orn) for Lys, Arg and His;
Citrulline (Cit) and methionine sulfoxide (MSO) for Thr, Asn and Gln;
N-methylphenylalanine (MePhe), trimethylphenylalanine, halo (F, Cl, Br and I) phenylalanine, triflourylphenylalanine, for Phe.

A useful method for identification of a residue of one of the sequences shown in SEQ ID Nos: 1, 2, 3, 4, 5 or 6 for amino acid substitution to generate a variant is called alanine scanning mutagenesis as described by Cunningham and Wells (1989) Science, 244:1081-1085. Here a residue or group of target residues are identified (eg charged residues such as Glu, Asp, Asn, Gln and Lys) and replaced by a neutral or negatively charged amino acid to affect the interaction of the amino acids with the surrounding environment. Those domains demonstrating functional sensitivity to the substitution then are refined by introducing further or other variations at or for the sites of substitution. Thus while the site for introducing an amino acid sequence variation is predetermined the nature of the mutation per se need not be predetermined. For example, to optimize the performance of a mutation at a given site, Ala scanning or random mutagenesis may be conducted at the target codon or region and the expressed peptide screened for the optimal combination of desired activity.

Phage display of protein or peptide libraries offers another methodology for the selection of peptide with improved or altered affinity, specificity, or stability (Smith, G, P, (1991) Curr Opin Biotechnol (2:668-673). High affinity proteins, displayed in a monovalent fashion as fusions with the M13 gene III coat protein (Clackson, T, (1994) et al, Trends Biotechnol 12:173-183), can be identified by cloning and sequencing the corresponding DNA packaged in the phagemid particles after a number of rounds of binding selection.

The peptides of the invention may be prepared as the free acid or base or converted to salts of various inorganic and organic acids and bases. Such salts are within the scope of this invention. Examples of such salts include ammonium, metal salts like sodium, potassium, calcium and magnesium; salts with organic bases like dicyclohexylamine, N-methyl-D-glucamine and the like; and salts with amino acids like arginine or lysine. Salts with inorganic and organic acids may be likewise prepared, for example, using hydrochloric, hydrobromic, sulfuric, phosphoric, trifluoroacetic, methanesulfonic, malic, maleic, fumaric and the like. Non-toxic and physiologically compatible salts are particularly useful, although other less desirable salts may have use in the processes of isolation and purification.

The peptide may include at least one carbohydrate molecule and/or at least one lipid molecule.

The peptide may include at least one alkyl group.

One particular application of the peptides of the invention is their use to provide fusion proteins that permit expression of a heterologous peptide on Gram-positive bacteria such as *Lactobacillus, Lactococcus, Bifidobacterium, Leuconostoc* and *Streptococcus* on the surface of these bacteria, or in culture supernatant derived therefrom.

Fusion proteins can be made by the chemical synthesis methods described below, or they can be made by recombinant DNA techniques, for example, wherein a nucleic acid molecule encoding the peptide having a sequence shown in one of SEQ ID Nos: 1, 2, 3, 4, 5 or 6 is arranged in a vector with a gene encoding a heterologous protein. Expression of the vector results in the peptide of the invention being produced as a fusion with the heterologous protein.

Three broad classes of fusion proteins are contemplated. The first class is that wherein the fusion protein includes a peptide having a sequence shown in one of SEQ ID Nos: 1, 2, 3, 4, 5 or 6 and a heterologous protein, wherein the heterologous protein is an antibody fragment or another high affinity molecule. These fusion proteins may have application as follows: in binding to and inactivating microbial toxins; binding to and blocking pathogenic microbe colonisation determinants such as fimbriae, non-fimbrial adhesins or other cell surface molecules involved in the virulence process; binding to and blocking host molecules that serve as receptors for pathogenic microorganisms; directly killing microorganisms; binding to cancer cells for the purpose of docking a chemotherapy compound; as in-vitro diagnostic reagents for use in e.g. ELISA assays; as in-vivo diagnostic reagents i.e. visualisation of a diagnostic target in a living body; or as immunohistochemistry reagents. Examples of heterologous proteins within this class include those described in: Kruger C, Hu Y, Pan Q, Marcotte H, Hultberg A, Delwar D, van Dalen P J, Pouwels P H, Leer R J, Kelly C G, van Dollenweerd C, Ma J K, Hammarstrom L In situ delivery of passive immunity by lactobacilli producing single-chain antibodies. Nat. Biotechnol. 2002 July; 20(7):702-6; Oggioni M R, Beninati C, Boccanera M, Medaglini D, Spinosa M R, Maggi T, Conti S, Magliani W, De Bernardis F, Teti G, Cassone A, Pozzi G, Polonelli L. Recombinant *Streptococcus gordonii* for mucosal delivery of a scFv microbicidal antibody. Int Rev Immunol. 2001; 20(2):275-87; Souriau C, Hudson P J. Recombinant antibodies for cancer diagnosis and therapy. 2003 Expert Opin Biol Ther April; 3(2):305-18; Ross J S, Gray K, Gray G S, Worland P J, Rolfe M. Anticancer antibodies. Am J Clin Pathol. 2003 April; 119(4):472-85; Kreitman R J. Recombinant toxins for the treatment of cancer. Curr Opin Mol. Ther. 2003 February; 5(1):44-51.

The second class is that wherein the fusion protein includes a peptide having a sequence shown in one of SEQ ID Nos: 1, 2, 3, 4, 5 or 6 and a heterologous protein, wherein the heterologous protein is a lysin, such as a phage lysin. These are particularly useful for specifically killing bacterial cells by disrupting the cell wall. Examples of lysins within this class include those described in:

Fischetti V A. Novel method to control pathogenic bacteria on human mucous membranes Ann N Y Acad. Sci. 2003 April; 987:207-14; Schuch R, Nelson D, Fischetti V A. A bacteriolytic agent that detects and kills *Bacillus anthracis*. Nature. 2002 August 22;418(6900):884-9; Loeffler J M, Fischetti V A. Synergistic lethal effect of a combination of phage lytic enzymes with different activities on penicillin-sensitive and -resistant *Streptococcus pneumoniae* strains. Antimicrob Agents Chemother. 2003 January; 47(1):375-7; Gaeng S, Scherer S, Neve H, Loessner M J. 2000. Gene cloning and expression and secretion of *Listeria monocytogenes* bacteriophage-lytic enzymes in *Lactococcus lactis*. Appl Environ Microbiol 66:2951-8.

The third class is that wherein the fusion protein includes a peptide having a sequence shown in one of SEQ ID Nos: 1, 2, 3, 4, 5 or 6 and a heterologous protein, wherein the heterologous protein is capable of eliciting a protective immune response against infection and disease. Examples of heterologous proteins within this class includes those described in: B. Smith D J, King W F, Barnes L A, Peacock Z, Taubman M A Immunogenicity and protective immunity induced by synthetic peptides associated with putative immunodominant regions of *Streptococcus mutans* glucan-binding protein. Infect Immun. 2003 March; 71(3):1179-84; Olive C, Clair T, Yarwood P, Good M F. Protection of mice from group A streptococcal infection by intranasal immunisation with a peptide vaccine that contains a conserved M protein B cell epitope and lacks a T cell autoepitope. Vaccine. 2002 Jun. 21;20(21-22):2816-25; Souza Fernandes R C, Sousa de Macedo Z, Medina-Acosta E Expression and purification of the recombinant enteropathogenic *Escherichia coli* vaccine candidates BfpA and EspB. Protein Expr Purif. 2002 June; 25(1):16-22; Pal S, Davis H L, Peterson E M, de la Maza L M Immunization with the *Chlamydia trachomatis* mouse pneumonitis major outer membrane protein by use of CpG oligodeoxynucleotides as an adjuvant induces a protective immune response against an intranasal chlamydial challenge. Infect Immun. 2002 September; 70(9):4812-7.

It will be understood that the invention contemplates the use of a peptide having a sequence shown in one of SEQ ID Nos: 1, 2, 3, 4, 5 or 6 with any heterologous protein, irrespective of the function of the heterologous protein. Particularly useful are heterologous proteins involved in the induction of immune tolerance and other modifications of immune system function, and the direct inhibition of pathogen binding using a non-immunoglobulin protein. Specific examples include a fusion protein having a sequence shown in one of SEQ ID Nos: 1, 2, 3, 4, 5, or 6 and (i) the der p1 antigen from the house dust mite; or (ii) the interleukin 1 receptor antagonist; or (iii) cyanovirin N; and interleukin 2 or γ interferon together with a heterologous protein to be used as a vaccine.

Fusion proteins can be cleaved using chemicals, such as cyanogen bromide, which cleaves at a methionine, or hydroxylamine, which cleaves between an Asn and Gly residue. Using standard recombinant DNA methodology, the nucleotide base pairs encoding these amino acids may be inserted just prior to the 5' end of the gene encoding the desired peptide.

Alternatively, one can employ proteolytic cleavage of fusion protein, see for example Carter in *Protein Purification: From Molecular mechanisms to Large-Scale Processes*, Ladisch et al., eds. (American Chemical Society Symposium Series No. 427, 1990), Ch 13, pages 181-193.

Proteases such as Factor Xa, thrombin, and subtilisin or its mutants, and a number of others have been successfully used to cleave fusion proteins. Typically, a peptide linker that is amenable to cleavage by the protease used is inserted between the further proteins (e.g., the Z domain of protein A) and the peptide of the invention. Using recombinant DNA methodology, the nucleotide base pairs encoding the linker are inserted between the genes or gene fragments coding for the other proteins. Proteolytic cleavage of the partially purified fusion protein containing the correct linker can then be carried out on either the native fusion protein, or the reduced or denatured fusion protein.

The peptide of the invention may not be properly folded when expressed as a fusion protein. Also, the specific peptide linker containing the cleavage site may or may not be accessible to the protease. These factors determine whether the fusion protein must be denatured and refolded, and if so, whether these procedures are employed before or after cleavage.

When denaturing and refolding are needed, typically the peptide is treated with a chaotrope, such as guanidine HCl, and is then treated with a redox buffer, containing, for example, reduced and oxidized dithiothereitol or glutathione at the appropriate ratios, pH, and temperature, such that the peptide is refolded to its native structure.

Other fusion proteins of the invention include those wherein the peptide of the invention is fused to a protein having a long half-life such as immunoglobulin constant region or other immunoglobulin regions, albumin, or ferritin.

Examples of ways of making fusion proteins are described further herein.

The peptides of the invention described above can be made by chemical synthesis or by employing recombinant DNA technology. These methods are known in the art. Chemical synthesis, especially solid phase synthesis, is preferred for short (e.g., less than 50 residues) peptides or those containing unnatural or unusual amino acids such as D-Tyr, Ornithine, amino adipic acid, and the like. Recombinant procedures are preferred for longer peptides. When recombinant procedures are selected, a synthetic gene may be constructed de novo or a natural gene may be mutated by, for example, cassette mutagenesis. These procedures are described further herein. Set forth below are exemplary general procedures for chemical synthesis of peptides of the invention.

Peptides are typically prepared using solid-phase synthesis, such as that generally described by Merrifield, J. *Am. Chem. Soc.,* 85: 2149 (1963), although other equivalent chemical syntheses known in the art are employable. Solid-phase synthesis is initiated from the C-terminus of the peptide by coupling a protected α-amino acid to a suitable resin. Such a starting material can be prepared by attaching a α-amino-protected amino acid by an ester linkage to a chloromethylated resin or a hydroxymethyl resin, or by an amide bond to a BHA resin or MBHA resin. The preparation of the hydroxymethyl resin is described by Bodansky et al., *Chem. Ind.* (*London*), 38: 1597-1598 (1966). Chloromethylated resins are commercially available from BioRad Laboratories, Richmond, Calif. And from Lab. Systems, Inc. The preparation of such a resin is described by Stewart et al., "Solid Phase Peptide Synthesis" (freeman & Co., San Francisco 1969), Chapter 1, pp. 1-6. BHA and MBHA resin supports are commercially available and are generally used only when the desired polypeptide being synthesized has an unsubstituted amide at the C-terminus.

The amino acids are coupled to the peptide chain using techniques well known in the art for the formation of peptide bonds. One method involves converting the amino acid to a derivative that will render the carboxyl group more susceptible to reaction with the free N-terminal amino group of the peptide fragment. For example, the amino acid can be converted to a mixed anhydride by reaction of a protected amino acid with ethychloroformate, phenyl chloroformate, sec-butyl chloroformate, isobutyl chloroformate, pivaloyl chloride or like acid chlorides. Alternatively, the amino acid can be converted to an active ester such as a 2,4,5-trichlorophenyl ester, a pentachlorophenyl ester, a pentafluorophenyl ester, a p-nitrophenyl ester, a N-hydroxysuccinimide ester, or an ester formed from 1-hydroxybenzotriazole.

Another coupling method involves use of a suitable coupling agent such as N,N$^1$-dicyclohexylcarbodiimide or N,N$^1$-diisopropylcarbodiimide. Other appropriate coupling agents, apparent in those skilled in the art, are disclosed in E Gross & J Meienhofer, *The Peptides: Analysis, Structure, Biology*, Vol. I: Major Methods of Peptide Bond Formation (Academic Press, New York, 1979).

It should be recognized that the α-amino group of each amino acid employed in the peptide synthesis must be protected during the coupling reaction to prevent side reactions involving their active amino function. It should also be recognized that certain amino acids contain reactive side-chain functional groups (eg sulfhydryl, amino, carboxyl, and hydroxyl) and that such functional groups must also be protected with suitable protecting groups to prevent a chemical reaction from occurring at that site during both the initial and subsequent coupling steps. Suitable protecting groups, known in the art, are described in Gross and Meienhofer, *The Peptides: Analysis, Structure, Biology*, Vol. 3: "Protection of Functional Groups in Peptide Synthesis" (Academic Press, New York 1981).

In the selection of a particular side-chain protecting group to be used in synthesizing the peptides, the following general rules are followed. An α-amino protecting group must render the α-amino function inert under the conditions employed in the coupling reacting, must be readily removable after the coupling reaction under conditions that will not remove side-chain protecting groups and will not alter the structure of the peptide fragment, and must eliminate the possibility of racemization upon activation immediately prior to coupling. A side-chain protecting group must render the side chain functional group inert under the conditions employed in the coupling reaction, must be stable under the conditions employed in removing the α-amino protecting group, and must be readily removable upon completion of the desired amino acid peptide under reaction conditions that will not alter the structure of the peptide chain.

It will be apparent to those skilled in the art that the protecting groups known to be useful for peptide synthesis will vary in reactivity with the agents employed for their removal. For example, certain protecting groups such as triphenylmethyl and 2-(p-biphenylyl)isopropyloxycarbonyl are very labile and can be cleaved under mild acid conditions. Other protecting groups, such as t-butyloxycarbonyl (BOC), t-amyloxycarbonyl, adamantyloxycarbonyl, and p-methoxybenzyloxycarbonyl are less labile and require moderately strong acid, such as trifluoroacetic, hydrochloric, or boron trifluoride in acetic acid, for their removal. Still other protecting groups, such as benzyloxy-carbonyl (CBZ or Z), halobenzyloxycarbonyl, p-nitrobenzyloxycarbonyl cycloalkyloxycarbonyl, and isopropyloxycarbonyl, are even less labile and require stronger acids, such as hydrogen fluoride, hydrogen bromide, or boron trifluoroacetate in trifluoroacetic acid, for their removal. Among the classes of useful amino acid protecting groups are included:

(1) for an α-amino group, (a) aromatic urethane-type protecting groups, such as fluorenylmethyloxycarbonyl (FMOC) CBZ, and substituted CBZ, such as, eg, p-chlorobenzyloxycarbonyl, p-6-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; (b) aliphatic urethane-type protecting groups, such as BOC, t-amyloxycarbonyl, isopropyloxycarbonyl, 2-(p-biphenylyl)-isopropyloxycarbonyl, allyloxycarbonyl and the like; (c) cycloalkyl urethane-type protecting groups, such as cyclopentyloxycarbonyl, adamantyloxycarbonyl, and cyclohexyloxycarbonyl; and (d) allyloxycarbonyl. The preferred α-amino protecting groups are BOX or FMOC.

(2) for the side chain amino group present in Lys, protection may be by any of the groups mentioned above in (1) such as BOC, p-chlorobenzyloxycarbonyl, etc.

(3) for the guanidino group of Arg, protection may be by mitro, tosyl, CBZ, adamantyloxycarbonyl, 2,2,5,7,8-pentamethylchroman-6-sulfonyl or 2,3,6-trimethyl-4-methoxyphenylsulfonyl, or BOC.

(4) for the hydroxyl group of Ser, Thr, or Tyr, protection may be, for example, by C1-C4 alkyl, such as t-butyl; benzyl (BAL); substituted BZL, such as p-methoxybenzyl, p-nitrobenzyl, p-chlorobenzyl, o-chlorobenzyl, and 2,6-dichlorobenzyl.

(5) for the carboxyl group of Asp or Glu, protection may be, for example, by esterification using groups such as BZL, t-butyl, cyclohexyl, cyclopentyl, and the like.

(6) for the imidazole nitrogen of His, the tosyl moiety is suitable employed.

(7) for the phenolic hydroxyl group of Tyr, a protecting group such as tetrahydropyranyl, tert-butyl, trityl, BZL, chlorobenzyl, 4-bromobenzyl, or 2,6-dichlorobenzyl is suitably employed. The preferred protecting group is 2,6-dichlorobenzyl.

(8) for the side chain amino group of Asn or Gln, xanthyl (Xan) is preferably employed.

(9) for Met, the amino acid is preferably left unprotected

(10) for the thio group of Cys, p-methoxybenzyl is typically employed.

The C-terminal amino acid, eg, Lys, is protected at the N-amino position by an appropriately selected protecting group, in the case of Lys, BOC. The BOC-Lys-OH can be first coupled to the benzyhydrylamine or chloromethylated resin according to the procedure set forth in Horiki et al, *Chemistry Letters*, 165-168 1978) or using isopropylcarbodiimide at about 25° C. for 2 hours with stirring. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups are described in the literature.

After removal of the amino protecting group, the remaining α-amino and side-chain protected amino acids are coupled stepwise within the desired order. As an alternative to adding each amino acid separately in the synthesis, some may be coupled to one another prior to addition to the solid-phase synthesizer. The selection of an appropriate coupling reagent is within the skill of the art. Particularly suitable as a coupling reagent is N,N$^1$-dicyclohexyl carbodiimide or diisopropylcarbodiimide.

Each protected amino acid or amino acid sequence is introduced into the solid-phase reactor in excess, and the coupling is suitably carried out in a medium of dimethylformamide (DMF) or CH$_2$Cl$_2$ or mixtures thereof. If incomplete coupling occurs, the coupling procedure is repeated before removal of the N-amino protecting group prior to the coupling of the next amino acid. The success of the coupling reaction at each stage of the synthesis may be monitored. A preferred method of monitoring the synthesis is by the ninhydrin reaction, as described by Kaiser et al., *Anal Biochem*, 34: 595 (1970). The coupling reactions can be performed automatically using well known methods, for example, a BIOSEARCH 9500™ peptide synthesizer.

Upon completion of the desired peptide sequence, the protected peptide must be cleaved from the resin support, and all protecting groups must be removed. The cleavage reaction and removal of the protecting groups is suitably accomplished simultaneously or stepwise. When the resin support is a chloromethylated polystyrene resin, the bond anchoring the peptide to the resin is an ester linkage formed between the free carboxyl group of the C-terminal residue and one of the many chloromethyl groups present on the resin matrix. It will be appreciated that the anchoring bond can be cleaved by reagents that are known to be capable of breaking an ester linkage and of penetrating the resin matrix.

One especially convenient method is by treatment with liquid anhydrous hydrogen fluoride. This reagent not only will cleave the peptide from the resin but also will remove all protecting groups. Hence, use of this reagent will directly afford the fully deprotected peptide. When the chloromethylated resin is used, hydrogen fluoride treatment results in the formation of the free peptide acids. When the benzhydrylamine resin is used, hydrogen fluoride treatment results directly in the free peptide amines. Reaction with hydrogen fluoride in the presence of anisole and dimethylsulfide at 0° C. for one hour will simultaneously remove the side-chain protecting groups and release the peptide from the resin.

When it is desired to cleave the peptide without removing protecting groups, the protected peptide-resin can undergo methanolysis to yield the protected peptide-resin can undergo methanolysis to yield the protected peptide in which the C-terminal carboxyl group is methylated. The methyl ester is then hydrolysed under mild alkaline conditions to give the free C-terminal carboxyl group. The protecting groups on the peptide chain then are removed by treatment with a strong acid, such as liquid hydrogen fluoride. A particularly useful technique for methanolysis is that of Moore et al, *Peptides, Proc Fifth Amer Pept Symp*, M Goodman and J Meienhofer, Eds, (John Wiley, N.Y., 1977), p. 518-521, in which the protected peptide-resin is treated with methanol and potassium cyamide in the presence of crown ether.

Another method of cleaving the protected peptide form the resin when the chloromethylated resin is employed is by ammonolysis or by treatment with hydrazine. If desired, the resulting C-terminal amide or hydrazide can be hydrolysed to the free C-terminal carboxyl moiety, and the protecting groups can be removed conventionally.

It will also be recognized that the protecting group present on the N-terminal α-amino group may be removed preferentially either before or after the protected peptide is cleaved from the support.

If in the peptides being created carbon atoms bonded to four non identical substituents are asymmetric, then the compounds may exist as disastereoisomers, enantiomers or mixtures thereof. The syntheses described above may employ racemates, enantiomers or disastereoisomers as starting materials or intermediates. Disastereomeric products resulting from such syntheses may be separated by chromatographic or crystallization methods. Likewise, enantiomeric product mixtures may be separated using the same techniques or by other methods known in the art. Each of the asymmetric carbon atoms, when present, may be in one of two configurations (R or S) and both are within the scope of the present invention.

Purification of the peptide is typically achieved using conventional procedures such as preparative HPLC (including reversed phase HPLC) or other known chromatographic techniques such as gel permeation, ion exchange, partition chromatography, affinity chromatography (including monoclonal antibody columns) or counter-current distribution.

As described above, the peptide of the invention may be prepared as salts of various inorganic and organic acids and bases. A number of methods are useful for the preparation of these salts and are known to those skilled in the art. Examples include reaction of the free acid or free base form of the peptide with one or more molar equivalents of the desired acid or base in a solvent or solvent mixture in which the salt is insoluble; or in a solvent like water after which the solvent is removed by evaporation, distillation or freeze drying. Alternatively, the free acid or base form of the produce may be passed over an ion-exchange resin to form the desired salt or one salt form of the product may be convened to another using the same general process.

The starting materials required for use in the chemical synthesis of peptides described above are known in the literature or can be prepared using known methods and known starting materials.

The invention also provides a nucleic acid molecule that encodes a peptide according to the invention.

In one aspect, the nucleic acid molecule encodes a peptide having a sequence shown in one of SEQ ID Nos: 1, 2, 3, 4, 5 or 6.

Typically, the nucleic acid molecule of the invention includes one of the sequences shown in SEQ ID Nos: 7, 8, 9, 10, 11, 12, 13, 14, 15, 16, 17, or 18, 19 or 20 or a sequence that is complementary to one of the sequences shown in SEQ ID Nos: 7, 8, 9, 10, 11, 12, 13, 14, 15, 16, 17, 18, 19 or 20.

A nucleic acid molecule that can hybridise to a molecule having one of the above described nucleotide sequences in high stringency conditions is particularly useful as the complementary strand of this nucleic acid molecule may well encode a peptide of the invention that is a variant. As is well known in the art, hybridisation of nucleic acid molecules may be controlled by the type of buffer used for hybridisation and the temperature of the buffer. "High stringency conditions" are conditions in which the buffer includes about 0.1×SSC, 0.1% SDS and the temperature is about 60° C.

The above described nucleic acid molecules can be obtained from genomic DNA, for example by PCR amplification, from a genomic library, from cDNA derived from mRNA, from a cDNA library, or by synthetically constructing the DNA sequence using synthetically derived nucleotides; (Sambrook et al., *Molecular Cloning: A Laboratory Manual* (2d ed.), Cold Spring Harbour laboratory, N.Y., 1989).

The nucleic acid molecule of the invention may be a deoxyribonucleotide, a ribonucleotide, a peptide nucleic acid or a combination thereof.

The invention also provides a vector or construct including a nucleic acid molecule of the invention.

A vector containing a sequence shown in SEQ ID NO 19 or 20 is particularly useful for expression of peptides of the invention and fusion proteins including a heterologous protein, as these sequences regulate expression in Gram-positive bacteria such as *Lactobacillus* and *Lactococcus*.

The vector or construct is typically obtained by inserting a nucleic acid molecule of the invention into an appropriate plasmid or vector which can be used to transform a cell, for example, a host cell. In general, plasmid vectors containing replication and control sequences which are derived from species compatible with the host cell are used in connection with those hosts. The vector ordinarily carries a replication site, as well as sequences which encode proteins or peptides that are capable of providing phenotypic selection in transformed cells.

Particularly preferred are vectors that permit the introduction of a nucleic acid molecule into Gram-positive bacteria such as *Lactobacillus, Lactococcus, Bifidobacterium, Leuconostoc* and *Streptococcus*. Examples of these vectors are described further herein.

A vector that may be useful for preparing, for example fusion protein constructs is pBR322 and derivatives thereof. pBR322 is a plasmid derived from an *E. coli* species, see for example Mandel et al., *J. Mol. Biol.* 53: 154 (1970). Plasmid pBR322 contains genes for ampicillin and tetracycline resistance and thus provides for easy means for selection. Other vectors include different features such as different promoters, which are often important in expression. For example, plasmids pKK223-3, pDR720, and pPL-lambda represent expression vectors with the tac, trp, or $P_L$ promoters that are currently available (Pharmacia Biotechnology).

A useful vector is pB0475. This vector contains origins of replication for phage and *E. coli* that allow it to be shuttled between such host, thereby facilitating both mutagenesis and expression, see for example, Cunningham et al., *Science,* 243: 1330-1336 (1989); U.S. Pat. No. 5,580,723. Other useful vectors are pR1T5 and pR1T2T (Pharmacia Biotechnology). These vectors contain appropriate promoters followed by the Z domain of protein A, allowing genes inserted into the vectors to be expressed as fusion proteins.

Other useful vectors can be constructed using standard techniques by combining the relevant traits of the vectors described above. Relevant traits include the promoter, the ribosome binding site, the decorsin or ornatin gene or gene fusion (the Z domain of protein A and decorsin or ornatin and its linker), the antibiotic resistance markers, and the appropriate origins of replication.

The invention also provides a cell including a vector or construct as described above. The host cell is typically prokaryotic and typically is a Gram-positive bacteria such as *Lactobacillus, Lactococcus, Bifidobacterium, Leuconostoc* or *Streptococcus*. Examples are shown in Table 2.

TABLE 2

| Bacterium | Current uses |
| --- | --- |
| Lactobacillus johnsonii La1 | Probiotic in yoghurt |
| Lactobacillus acidophilus | Probiotic in yoghurt |
| Lactobacillus casei Shirota | Probiotic in yoghurt |
| Lactobacillus reuteri | Probiotic in yoghurt |
| Bifidobacterium longum | Probiotic in yoghurt |
| Bifidobacterium bifidum | Probiotic in yoghurt |
| Leuconostoc mesenteroides | Sauerkraut fermentation |
| Streptococcus thermophilus | Yoghurt and cheese making |

Prokaryotes may be used for cloning and expressing a nucleic acid molecule of the invention to produce the peptide of the invention. For example, *E. coli* K12 strain 294 (ATCC No. 31446) may be used as well as *E. coli* B, *E. coli* X1776 (ATC No. 31537), and *E. coli* c600 and c600hfl, *E. coli* W3110 (F-,gama-,prototrophic/ATCC No. 27325), bacilli such as *Bacillus subtilis*, and other Enterobacteriaceae such as *Salmonella_typhimurium* or *Serratia marcesans*, and various *Pseudomonas* species. When expressed by prokaryotes the peptide of the invention may contain an N-terminal methionine or a formyl methionine and may not be glycosylated. In the case of fusion proteins, the N-terminal methionine or formyl methionine may reside on the amino terminus of the fusion protein or the signal sequence of the fusion protein.

The invention also provides a process for producing a peptide of the invention. The process includes maintaining a cell containing a nucleic acid molecule as described above, or a vector or construct as described above, in conditions for permitting the cell to produce the peptide.

The process may optionally include the step of recovering and or purifying the protein. Purification of the peptide is typically achieved using conventional procedures such as preparative HPLC (including reversed phase HPLC) or other known chromatographic techniques such as gel permeation, ion exchange, partition chromatography, affinity chromatography (including monoclonal antibody columns) or countercurrent distribution.

The expression of a peptide of the invention is described further herein. Other exemplary expression systems include those described in Table 3 below.

TABLE 3

| Expression system | | Reference |
| --- | --- | --- |
| NICE system | Uses the a promoter inducible by the food preservative antimicrobial peptide nisin. Used in *Lactobacillus, Leuconostoc* & *Lactococcus*. | Kleerebezem et al., 1997 |
| T7 system | Uses the strong T7 RNA polymerase. Used in *Lactococcus*. | Wells et al., 1993 |
| Lactose-induction | Uses the lactose inducible promoter of the lactose operon from *Lactobacillus casei*. Used in *Lactobacillus casei*. | Perez-Arellano et al., 2003 |
| S-layer promoter | Uses the strong promoter of *Lactobacillus brevis*. Used in *Lactobacillus* and *Lactococcus*. | Savijoki et al., 1997 |
| pTUAT vector | Uses the amy promoter which is induced with mannitol. Used in *Lactobacillus*. | Kruger et al., 2002 |

Kleerebezem M, Beerthuyzen M M, Vaughan E E, de Vos W M, Kulpers O P. Controlled gene expression systems for lactic acid bacteria: transferable nisin-inducible expression cassettes for *Lactococcus, Leuconostoc*, and *Lactobacillus* spp. Appl Environ Microbiol. 1997 November; 63(11):4581-4; Kruger C, Hu Y, Pan Q, Marcotte H, Hultberg A, Delwar D, van Dalen P J, Pouwels P H, Leer R J, Kelly C G, van Dollenweerd C, Ma J K, Hammarstrom L. In situ delivery of passive immunity by lactobacilli producing single-chain antibodies. Nat. Biotechnol. 2002 July;20(7):702-6; Perez-Arellano I, Perez-Martinez G. Optimization of the green fluorescent protein (GFP) expression from a lactose-inducible promoter in *Lactobacillus casei*. FEMS Microbiol Lett. 2003 May 16; 222(1):123-7; Savijoki K, Kahala M, Palva A. High level heterologous protein production in *Lactococcus* and *Lactobacillus* using a new secretion system based on the *Lactobacillus brevis* S-layer signals. Gene. 1997 Feb. 28; 186(2):255-62; Wells J M, Wilson P W, Norton P M, Gasson M J, Le Page R W. *Lactococcus lactis*: high-level expression of tetanus toxin fragment C and protection against lethal challenge. Mol Microbiol. 1993 June; 8(6):1155-62.

BRIEF DESCRIPTION OF THE DRAWINGS

FIG. 8. Sep LysM domain amino acid sequence (SEQ ID NO:1).

FIG. 9. Sep C-terminal (apf) domain amino acid sequence (SEQ ID NO:2).

FIG. 10. Sep glutamine-rich region (SEQ ID NO:3).

FIG. 11. Sep secretion signal amino acid sequence (SEQ ID NO:4).

FIG. 12. Sep amino acid sequence (SEQ ID NO:5).

FIG. 13. Sep amino acid sequence including secretion signal sequence ((SEQ ID NO:6).

FIG. 14. Sep secretion signal nucleotide sequence (SEQ ID NO:7). IUB Mixed Base Codes: R=AG Y=CT M=AC K=GT S=GC W=AT H=ACT B=GCT V=AGC D=AGT N=AGCT.

FIG. 15. Sep LysM domain nucleotide sequence (SEQ ID NO:8). IUB Mixed Base Codes: R=AG Y=CT M=AC K=GT S=GC W=AT H=ACT B=GCT V=AGC D=AGT N=AGCT.

FIG. 16. Sep glutamine-rich region nucleotide sequence (SEQ ID NO:9). IUB Mixed Base Codes: R=AG Y=CT M=AC K=GT S=GC W=AT H=ACT B=GCT V=AGC D=AGT N=AGCT.

FIG. 17. Sep C-terminal nucleotide sequence (SEQ ID NO:10). IUB Mixed Base Codes: R=AG Y=CT M=AC K=GT S=GC W=AT H=ACT B=GCT V=AGC D=AGT N=AGCT.

FIG. 18. Sep nucleotide sequence (SEQ ID NO:11). IUB Mixed Base Codes: R=AG Y=CT M=AC K=GT S=GC W=AT H=ACT B=GCT V=AGC D=AGT N=AGCT.

FIG. 19. Sep nucleotide sequence including secretion signal coding sequence (SEQ ID NO:12). IUB Mixed Base Codes: R=AG Y=CT M=AC K=GT S=GC W=AT H=ACT B=GCT V=AGC D=AGT N=AGCT.

FIG. 20. Sep secretion signal backtranslation sequence (SEQ ID NO:13). IUB Mixed Base Codes: R=AG Y=CT M=AC K=GT S=GC W=AT H=ACT B=GCT V=AGC D=AGT N=AGCT.

FIG. 21. Sep LysM domain signal backtranslation sequence (SEQ ID NO:14). IUB Mixed Base Codes: R=AG Y=CT M=AC K=GT S=GC W=AT H=ACT B=GCT V=AGC D=AGT N=AGCT.

FIG. 22. Sep glutamine-rich region signal backtranslation sequence (SEQ ID NO:15). IUB Mixed Base Codes: R=AG Y=CT M=AC K=GT S=GC W=AT H=ACT B=GCT V=AGC D-AGT N=AGCT.

FIG. 23. Sep C-terminal signal backtranslation sequence (SEQ ID NO:16). IUB Mixed Base Codes: R=AG Y=CT M=AC K=GT S=GC W=AT H=ACT B=GCT V=AGC D-AGT N=AGCT.

FIG. 24. Sep backtranslation sequence (SEQ ID NO:17). IUB Mixed Base Codes: R=AG Y=CT M=AC K=GT S=GC W=AT H=ACT B=GCT V=AGC D-AGT N=AGCT.

FIG. 25. Sep including secretion signal backtranslation sequence (SEQ ID NO:18). IUB Mixed Base Codes: R=AG Y=CT M=AC K=GT S=GC W=AT H=ACT B=GCT V=AGC D-AGT N=AGCT.

FIG. 26. Nucleotide sequence of 310-bp immediately upstream of sep containing a possible sep promoter (putative-35 and -10 recognition hexamers are indicated as shaded letters and bold letters respectively [note one –35 consensus also may be a –10 consensus]; TG motifs upstream of the putative –10 consensus hexamers are italicized; the sep ribosome binding site is underlined (SEQ ID NO:19). IUB Mixed Base Codes: R=AG Y=CT M=AC K=GT S=GC W=AT H=ACT B=GCT V=AGC D-AGT N=AGCT.

FIG. 27. Nucleotide sequence of 150-bp immediately downstream of sep containing sep transcription terminator (indicated as converging arrows above the sequence (SEQ ID NO:20). IUB Mixed Base Codes: R=AG Y=CT M=AC K=GT S=GC W=AT H=ACT B=GCT V=AGC D-AGT N=AGCT.

The invention is described below with reference to certain non-limiting examples. It will be appreciated by persons skilled in the art that numerous variations and/or modifications may be made to the invention as described without departing from the spirit or scope of the invention as broadly described. The following examples are, thereof, to be considered in all respects as illustrative and not restrictive.

EXAMPLE 1

Production of Sep

Figure 1:
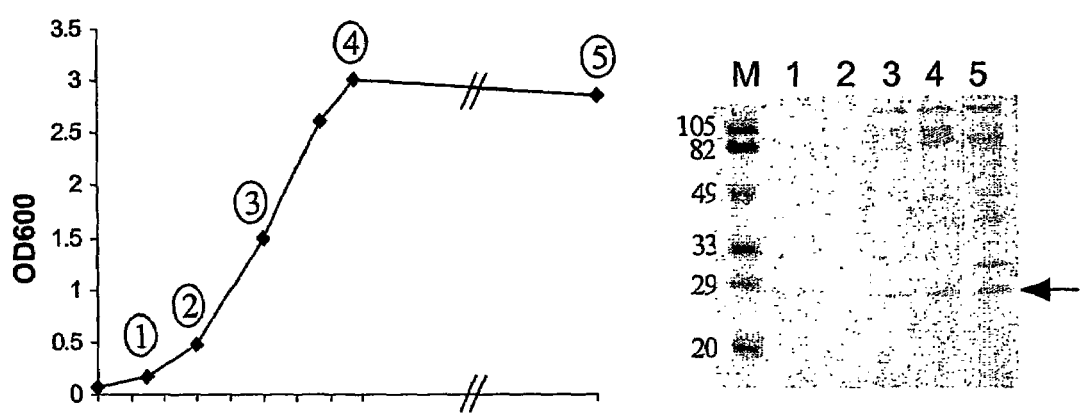
FIG. 1. Analysis of proteins found in the culture supernatant of *L. fermentum* BR11 grown in MRS broth. Growth of *L. fermenturn* BR11 was monitored over 24-h by optical density measurements at 600 nm. At various time points, indicated by a number in a ircle, aliquots were taken, centrifuged and the supernatant filtered and precipitated with 5% TCA. The equivalent of 225-µl of culture supernatant was analysed by SDS-PAGE followed by staining with Coomassie brilliant blue G-250. The arrow indicates Sep.

*L. fermentum* BR11 was grown in standing MRS broth at 37° C. and fractions were taken at five timepoints (FIG. 1). SDS-PAGE analysis revealed a number of proteins which accumulated in the supernatant during growth (FIG. 1). The smallest visible protein (indicated by the arrow) was still abundant in late stationary phase when the level of a number of other proteins had reduced. This protein was called Sep for small exported protein. When its small size is taken into account, Sep is one of the most abundant proteins found in the supernatant of *L. fermentum* BR11. To further characterise Sep we identified the N-terminal sequence which was found to be: DTIYTVQSGDTLSGI. (SEQ ID NO:34). Sep is a 205 amino acid protein with a 30 amino acid N-terminal secretion signal giving rise to a predicted 19-kDa mature protein with an isoelectric point of 5.3.

EXAMPLE 2

Sep-E Cadherin Fusion Protein Under Control of Sep Promoter

*Escherichia coli* JM109 was used in molecular cloning experiments. Ampicillin was used at a concentration of 100 or 200 µg per ml for *E. coli* while erythromycin was used at concentrations of 750 µg per ml for *E. coli*. Plasmids pUC18, pBluescriptII (KS) and pGEM3zf were used for routine cloning.

The region encoding the amino-terminal 1 to 216 amino acids of the mature E-cadherin protein was amplified by PCR from cDNA template prepared from cultured mammalian T47D and LNCap cells using oligonucleotides E-cad-PstI and E-cad-XhoI (Table 4: SEQ ID NOS: 32 and 33 respectively). This fragment was cloned in frame downstream of DNA encoding the Sep secretion signal to generate construct Sep-6xHis-Ecad. The sequence of the cloned E-cadherin DNA fragment which contained an introduced stop codon after codon 216 was checked by DNA sequencing. The putative bspA transcription terminator was amplified using oligonucleotides Term-Xho and Term-Hind and cloned downstream of the E-cadherin encoding DNA.

The construct within pJRS233 was transformed into *L. fermentum* BR11 using penicillin as a cell wall weakening agent at concentrations of 1 or 10 µg per ml, respectively, as described previously (Rush, C. M., L. M. Hafner, and P. Timms. 1994. Genetic modification of a vaginal strain of *Lactobacillus fermentum* and its maintenance within the reproductive tract after intravaginal administration. J. Med. Microbiol. 41:272-278; McCracken, A., M. S. Turner, P. Giffard, L. M. Hafner, and P. Timms. 2000. Analysis of promoter sequences from *Lactobacillus* and *Lactococcus* and their activity in several *Lactobacillus* species. Arch. Microbiol. 173:383-389). The construct was integrated into the chromosome of *L. fermentum* downstream of the sep promoter by incubating transformants at 40° C. in the presence of erythromycin selection.

*L. fermentum* BR11 were grown on solid MRS medium (Oxoid, Basingstoke, United Kingdom) anaerobically or in standing liquid culture tubes. Erythromycin was used at a concentration of 10 µg per ml for *L. furmentum*.

Cell extracts were prepared from late log or early stationary phase cultures while supernatants were taken from late exponential phase cultures. Two different whole cell protein extraction methods which involved either boiling cells in 2x SDS-PAGE loading buffer (Sambrook, J., E. F. Fritsch, and T. Maniatis. 1989. Molecular cloning: a laboratory manual, 2nd ed. Cold Spring Harbor Laboratory press, Cold Spring Harbor, N.Y.) or sonication were used as described previously (Turner, M. S., L. M. Hafner, T. Walsh, and P. M. Giffard. 2003. Peptide surface display and secretion using two LPXTG-containing surface proteins from *Lactobacillus fermentum* BR11. Appl. Environ. Microbiol. 69:5855-5863). 5M LiCl extractions of cells and supernatant fractions were also obtained as described previously (Turner 2003). Prior to loading of SDS-PAGE all samples were boiled for 5 minutes. Proteins were transferred to nitrocellulose, blocked and then probed with an anti-His$_5$ monoclonal antibody (Qiagen, Hilden, Germany) at 1 in 1000 dilution. Following washes, the membrane was incubated with rabbit anti-mouse-horseradish peroxidase (HRP) conjugate (Dako, Glostrop, Denmark). The bound antibodies were detected using the HRP chemiluminescence kit (Roche, Mannheim, Germany). To estimate levels of His$_6$ proteins in extracts varying amounts of His$_6$ labeled protein markers (Qiagen, Glostrop, Denmark) were included alongside the samples. These markers have known quantities of His$_6$ containing proteins in each band allowing densitometry to be done on films using the TotalLab v1.11 package (Phoretix, Newcastle upon Tyne, United Kingdom). For detection of E-cadherin a mouse monoclonal anti-human E-cadherin antibody (from clone HECD-1; Zymed Laboratories Inc.) was used at a concentration of 1 in 750.

Figure 2:
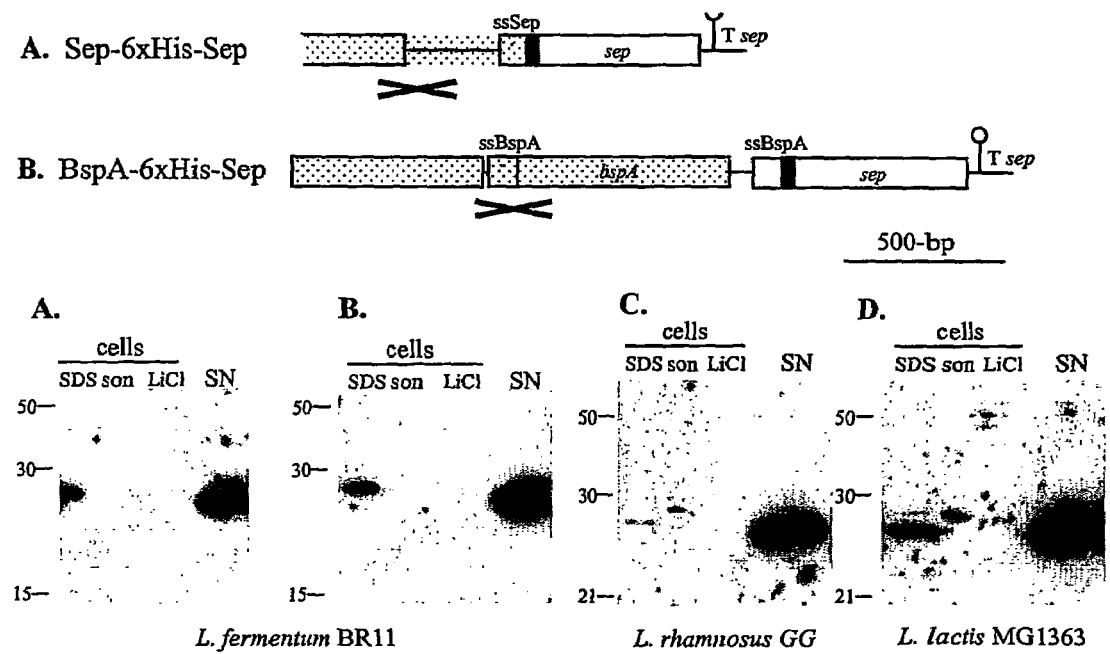
FIG. 2. Expression and subcellular location of a His$_6$-Sep protein in *L. fermentum* BR11, *L. rhamnosus* GG and *L. lactis* MG1363. Above shows the arrangement of the constructs which were either integrated into the *L. fermentum* BR11 chromosome (Sep-6×His-Sep and BspA-6×His-Sep) or introduced into *L. rhamnosus* GG or *L. lactis* MG1363 on the pGh9:ISS1 plasmid (Sep-6×His-Sep only). Below shows Western blot detection of fusion proteins in cell extracts and in the supernatant using an anti-His$_5$ antibody. For the diagrams the sep terminator (Tsep) and DNA encoding the Sep secretion signal (ssSep), BspA secretion signal (ssBspA) and His$_6$ (grey box) are indicated. The DNA region which is the site of single crossover homologous recombination into either the sep or bspA loci of *L. fermentum* BR11 is spotted and below is marked with a cross. Sizes of molecular mass markers are indicated in kDa on the left. The lanes containing cell extracts prepared by boiling in 2× SDS-loading dye (SDS), by sonication (son) and with 5M LiCl (LiCl) and the precipitated supernatant fractions (SN) are indicated. The amount of cells or medium loaded in each lane are the equivalent to 500 μl (SDS), 50 μl (son), 160 μl (LiCl) and 675 μl (SN) of culture.

E-cadherin fusion protein was detected in the SDS cell extract and supernatant from cells grown at 30° C. (FIG. 2). Levels of E-cadherin fusion protein for this strain at 30° C. were ~30 µg per liter culture in the supernatant and ~370 µg per liter in the SDS cell extract. The predicted size of the E-cadherin fusion protein is 25-kDa, however the protein recognized by the anti-His₅ antibody in the Western blot resolved ~38-kDa. To confirm that this protein is indeed E-cadherin, a mouse monoclonal anti-human E-cadherin antibody was used as the primary antibody in a Western blot. The anti-E-cadherin antibody recognized a protein the same size as the protein recognized using the anti-His₅ antibody and did not recognize proteins found in the supernatant of the parent *L. fermentum* BR11 strain. These results suggest that Sep expression and secretion signals can be used to secrete a human amino-terminal E-cadherin peptide in *L. fermentum*. As the amino-terminus of E cadherin is a major intestinal cell receptor for the food-borne disease causing pathogen *L. monocytogenes* this construct may have potential as an intestinal *L. monocytogenes* attachment-inhibiting therapeutic.

EXAMPLE 3

Sep-6xHis Fusion Proteins Under Control of Sep Promoter

*E. coli* JM109 was used in molecular cloning experiments. Ampicillin was used at a concentration of 100 or 200 μg per ml for *E. coli*. Plasmids pUC18, pBluescriptII (KS) and pGEM3zf were used for routine cloning.

The construct (Sep-6xHis-Sep) consists of DNA upstream of sep and the sep 5' region encoding the secretion signal and a six-histidine (His₆) epitope (amplified and cloned using Nterm-US-Xba (SEQ ID NO: 28) and Nterm-Pst-US) (SEQ ID NO: 29)) and DNA encoding the mature Sep protein and the putative sep transcription terminator (amplified and cloned using SepDS-PstXho (SEQ ID NO: 30) and SepDS-ApaSal (SEQ ID NO: 31)). The construct (BspA-6xHis-Sep) consists of DNA encoding the mature Sep protein and putative sep transcription terminator as above but instead contains upstream DNA encoding a full length BspA protein followed by DNA encoding the BspA secretion signal and a His6 epitope as described previously (Turner et al., supra). The extra amino acids added onto the mature N-termini of Sep in the Sep-6xHis-Sep construct are: DTIYTDHHHHHH-SAAGST (SEQ ID NO: 21) and in the BspA-6xHis-Sep construct are: ASDDVHHHHHHSAAGST (SEQ ID NO: 22).

These expression cassettes were constructed in pBluescriptII and then cloned into the XbaI and SalI digested pJRS233. The Sep-6xHis-Sep construct in pBluescript II is also digested with SalI and cloned into XhoI digested pGh9:ISS1.

The construct within pJRS233 was transformed into *L. fermentum* BR11 using penicillin as a cell wall weakening agent at concentrations of 1 or 10 μg per ml, respectively, as described previously (Rush, McCracken, supra). Expression in *L. fermentum* was achieved by integrating the chimeric genes downstream of either the sep or bspA promoters (FIGS. 3A and 3B) by incubating transformants at 40° C. in the presence of erythromycin selection.

*L. fermentum* BR11 was grown on solid MRS medium (Oxoid, Basingstoke, United Kingdom) anaerobically or in standing liquid culture tubes. Erythromycin was used at a concentration of 10 g per ml for *L. fermentum*.

In the cases of *L. rhamnosus* and *L. lactis*, the Sep-6xHis-Sep construct was transformed into the cells cloned into the pGh9:ISS1 plasmid (Maguin, E., H. Prevost, S. D. Ehrlich, and A. Gruss. 1996. Efficient insertional mutagenesis in lactococci and other gram-positive bacteria. J. Bacteriol. 178: 931-935).

*L. rhamnosus* GG (ATCC 53103) was grown on solid MRS medium (Oxoid, Basingstoke, United Kingdom) anaerobically or in standing liquid culture tubes. *L. lactis* MG1363 was grown at 30° C. in M17 medium (Oxoid, Basingstoke, United Kingdom) supplemented with 0.5% (wt/vol) glucose (GM17). Erythromycin is used at concentrations of 10 μg per ml for *L. rhamnosus* and 5 μg per ml for *L. lactis*.

Transformation of *L. rhamnosus* is done using penicillin as a cell wall weakening agent at concentrations of 1 or 10 μg per ml, respectively, as described previously (Rush, McCracken, 2000, supra). *L. lactis* is transformed using 1% glycine as a cell wall weakening agent as described previously (Holo, H., and I. F. Nes. 1989. High-frequency transformation, by electroporation, of *Lactococcus lactis* subsp. *cremoris* grown with glycine in osmotically stabilized media Appl. Environ. Microbiol. 55: 3119-3123), except transformants are selected directly on GM17 plates containing 5 μg per ml erythromycin. *L. lactis* transformants are grown at 30° C. to allow replication of the temperature sensitive pGh9:ISS1 plasmid derivatives while *L. rhamnosus* transformants are grown on plates at 30° C. and in liquid at 30° C. or 37° C.

Cell fractionation, protein extraction and Western blot analysis were performed as described in Example 2. The accessibility of the His₆ epitope on whole cells is done the same as that described previously (Turner 2003 supra).

Figure 3:
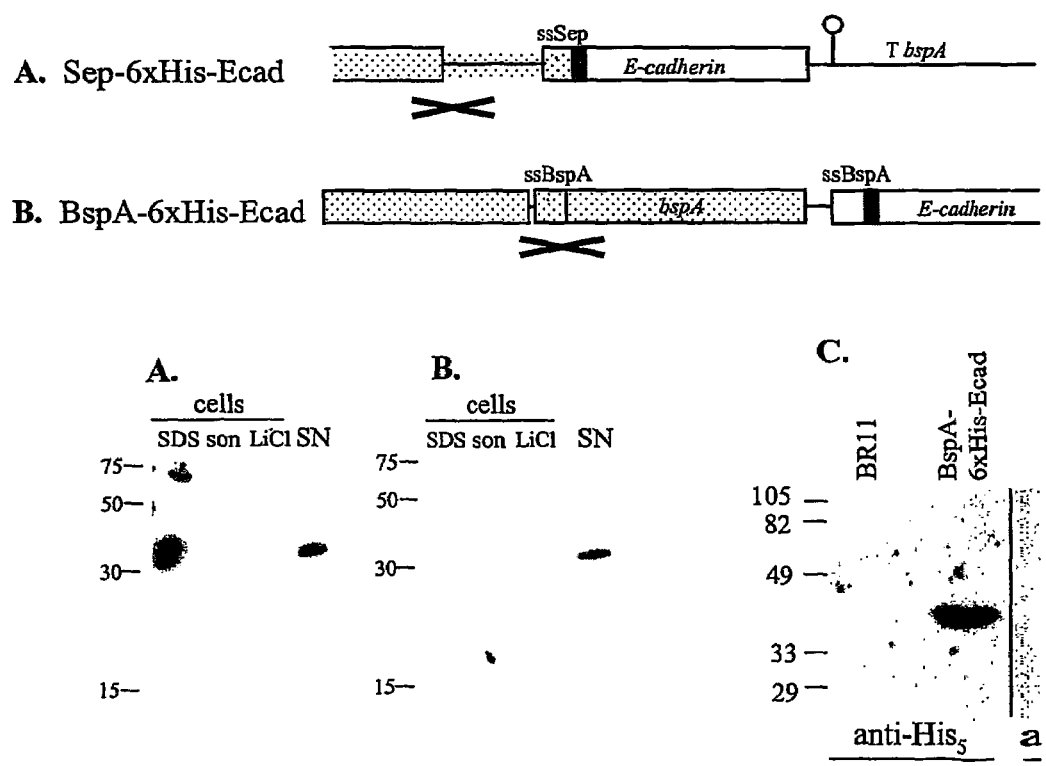
FIG. 3. Expression and secretion of human E-cadherin fusion protein by *L. fermentum* BR11. Above shows the arrangement of the constructs which were introduced into *L. fermentum* BR11 (Sep-6×His-Ecad and BspA-6×His-Ecad). Below shows Western blot detection of fusion proteins in cell extracts and in the supernatant using an anti-His$_5$ antibody (C[right side]). For the diagrams the bspA terminator (T bspA) and DNA encoding the Sep secretion signal (ssSep), BspA secretion signal (ssBspA) and His$_6$ (grey box) are indicated. The DNA region which is the site of single crossover homologous recombination into either the sep or bspA loci of *L. fermentum* BR11 is spotted and below is marked with a cross. The sizes of the molecular mass markers are indicated in kDA on the left. The lanes containing cell extracts prepared by boiling in 2× SDS-loading dye (SDS), by sonication (son) and with 5M LiCl (LiCl) and the precipitated supernatant fractions (SN) are indicated. The amount of cells or medium loaded in each lane are the equivalent to 500 μl (SDS), 50 μl (son), 160 μl (LiCl) and 675 μl (SN) of culture. For the Western blot in part C, the equivalent of 1.2-ml of culture supernatant form *L. fermentum* BR11 parent (BR11) or *L. fermentum* containing BspA-6×His-Ecad (BspA-6×His-Ecad) was located in each lane.

The predicted molecular mass of the mature His₆-Sep fusion proteins is 21-kDa, although the bands in Western blots correspond to proteins 28-kDa in size (FIGS. 3A and 3B). In *L. fermentum* containing the Sep-6xHis-Sep and the BspA-6xHis-Sep constructs the Sep fusion protein was found predominantly in the supernatant at levels of ~2 mg per liter of culture in both cases. Levels of the Sep fusion protein in the SDS cell extracts for *L. fermentum* containing the Sep-6xHis-Sep and BspA-6xHis-Sep constructs were ~9% and ~13% of that found in the supernatants, respectively. No Sep fusion protein was detected in sonicate or 5 M LiCl extracts. When SDS cell and supernatant extracts were run in neighbouring lanes the Sep fusion protein bands migrated identically on SDS-PAGE (data not shown), which suggests that the Sep fusion protein associated with cells is the mature form and therefore does not contain a signal sequence and is located outside the cytoplasmic membrane.

In *L. rhamnosus* and *L. lactis*, levels of Sep fusion protein expressed from the Sep-6xHis-Sep construct were found to be ~200 and ~300 μg per liter of culture in the supernatant, respectively (FIGS. 3C and 3D). Levels of the Sep fusion protein in the SDS cell extracts for *L. rhamnosus* and *L. lactis* were <1% and ~10% of that found in the supernatants, respectively. Interestingly a slightly larger molecular weight His₆ reactive protein was observed in the sonicate cell extracts of both *L. rhamnosus* and *L. lactis* and in the SDS cell extract of *L. lactis*. This band probably corresponds to Sep fusion protein still containing its secretion signal. Like *L. fermentum*, no His₆-Sep was detected in the 5 M LiCl extracts of either *L. rhamnosus* or *L. lactis* containing the Sep-6xHis-Sep construct.

To examine if Sep is exposed on the cell surface of *L. fermentum*, a whole cell enzyme-linked immunosorbent assay for the His₆ epitope was performed the same to that described previously (Turner et al., supra). It was found that the $A_{450nm}$ signal per $OD_{600\ nm}$ unit of cells obtained for *L. fermentum* cells containing the BspA-6xHis-Sep construct (0.0302±0.0003) was significantly greater (1.8-fold) than for *L. fermentum* BR11 cells (0.0168±0.0007). This result suggests that at least some cell associated Sep is located in an exposed form in the cell envelope of L. fermentum.

EXAMPLE 4

Expression of Human Vitronectin in Lactobacillus fermentum BR11 and Lactobacillus rhamnosus GG Using the Expression and Secretion Signals of Sep The expression construct used here utilises the Sep expression and secretion signals such that human vitronectin is exported into the culture supernatant from the host Lactobacillus. The mature vitronectin gene was amplified from cDNA and cloned into the Sep-6xHis-Ecad expression cassette using restriction enzymes PstI and XoI. Following its insertion into the pGh9::ISS1 plasmid, the hydrid was transformed into L. fermentum BR11 and L. rhamnosus GG. Following 2 days growth at 32° C., cells were fractionated and analysed using Western blot to detect $His_6$-tagged vitronectin.

The lanes containing cell extracts (C) prepared by boiling cells in 2x SDS-PAGE loading buffer and the precipitated supernatant fractions (S) are indicated. The amount of cells or medium loaded in each lane is the equivalent to 1 ml (C) and 900 µl (S) of culture.

Figure 4:
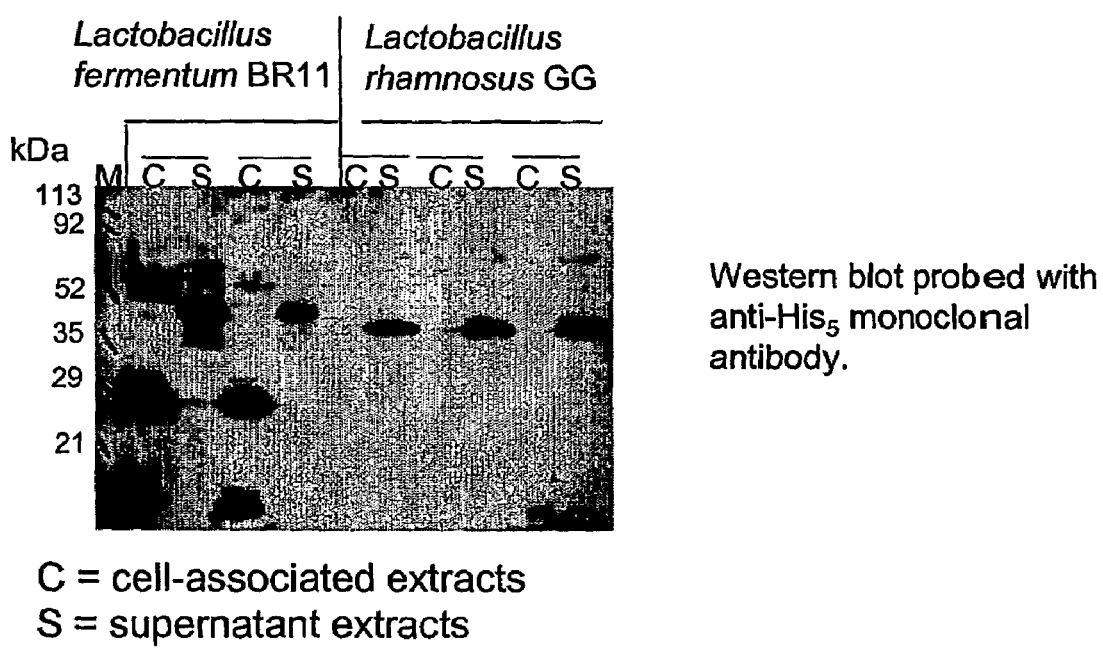
FIG. 4. Expression of human vitronectin using the expression and secretion signals of Sep. The lanes containing cell extracts (C) prepared by boiling cells in 2x SDS-PAGE loading buffer and the precipitated supernatant fractions (S) are indicated. The amount of cells or medium loaded in each lane is the equivalent to 1 ml (C) and 900 μl (S) of culture.

The predicted size of mature non-glycosylated His6-vitronectin is 54 kDa. For clones of L. fermentum BR11 there is a clear dominant protein ~52-kDa in the supernatant which probably corresponds to full-length vitronectin FIG. 4. The cell extracts of L. fermentum BR11 clones show a number of bands with the majority being smaller, probably degraded forms of vitronectin. For clones of L. rhamnosus GG there is one dominant band in the supernatant fraction which is ~47-kDa which probably corresponds to His6-vitronectin with a small amount of C-terminal degradation.

Therefore in conclusion Sep has been shown to express and secrete a large, cysteine-rich human protein of commercial importance in the generally regarded as safe lactobacilli.

EXAMPLE 5

Expression and Secretion of Active Listeria monocytogenes Bacteriophage A511 Endolysin Ply511 by Lactobacillus Material and Methods
Bacterial Strains, Plasmids and Growth Conditions L. fermentum BR11, L. rhamnosus GG (ATCC 53103) and L. plantarum ATCC 14917 were grown on solid MRS medium (Oxoid, Basingstoke, U.K.) anaerobically or in standing liquid culture tubes. L. lactis MG1363 was grown at 30° C. in M17 medium (Oxoid, Basingstoke, U.K.) supplemented with 0.5% (wt/vol) glucose (GM17) and when appropriate in the presence of erythromycin (GM17E). Escherichia coli JM109 was used in molecular cloning experiments. Ampicillin was used at a concentration of 100 or 200 µg per ml for E. coli while erythromycin was used at concentrations of 500-750 µg per ml for E. coli, 10 µg per ml for lactobacilli and 5 µg per ml for L. lactis. Expression cassettes were introduced into lactic acid bacteria using pGh9:ISS1. Plasmid pGEM3Zf was used for routine cloning.

Transformation of Lactobacilli and L. lactis

Transformation of L. fermentum, L. rhamnosus and L. plantarum was done using penicillin as a cell wall weakening agent at concentrations of 1.25, 10 and 5 µg per ml, respectively. L. lactis was transformed using 1% glycine as a cell wall weakening agent, except that transformants were selected directly on GM17 plates containing 5 µg per ml erythromycin. L. lactis transformants (containing pGh9:ISS1 derivatives) were grown at 30° C. while lactobacilli transformants (containing pGh9:ISS1 derivatives) were grown on plates and in liquid media at 32-33° C.

Construction of Ply511 into the Sep Secretion Expression Cassette

DNA encoding amino acids 1 to 341 of the endolysin Ply511 of L. monocytogenes phage A511 was amplified using cloned ply511 as template. This fragment was cloned in frame downstream of DNA encoding the Sep secretion signal in plasmid pGEM-3Zf containing the Sep-6xHis-Ecad expression construct such that the E-cadherin encoding gene fragment is replaced with the ply511 gene. The new plasmid was named pSep-6xHis-Ply511. The functional parts of the Sep-6xHis-Ply511 construct were amplified using oligonucleotides SepUS-Eco and Term-Hind-trunc and this 1.9-kb fragment was then digested with EcoRI and HindIII. This fragment was ligated to similarly digested pGh9::ISS1 (which removes the ISS1 insertion sequence) and the ligation mix was transformed directly into L. lactis. L. lactis transformants were plated onto GM17 agar containing 5 µg per ml erythromycin and sufficient autoclaved L. monocytogenes 491 cells to obtain visible turbidity. After 2 days clones secreting active Ply511 could be detected by the formation of clearing zone around the colonies. Plasmids from the positive clones were purified and were used to transform lactobacilli.

Cell Fractionation, Protein Extraction and Western Blot Analysis

Cell extracts and supernatants were prepared from late exponential or early stationary phase cultures. Cell extracts were prepared by boiling cells in 2x SDS-PAGE loading buffer and supernatants were concentrated using 5% trichloroacetic acid as described previously. Proteins were transferred to nitrocellulose, blocked and then probed with an anti-$His_5$-horseradish peroxidase (HRP) conjugate antibody (Qiagen, Hilden, Germany) at 1 in 4,000 dilution. The bound antibodies were detected using the Lumi-Light chemiluminescence kit (Roche, Mannheim, Germany). To estimate levels of $His_6$ proteins in extracts, varying amounts of $His_6$ labeled protein markers (Qiagen, Glostrop, Denmark) were included alongside the samples. These markers have known quantities of $His_6$ containing proteins in each band allowing densitometry to be done on films using the TotalLab v1.11 package (Phoretix, Newcastle upon Tyne, U.K.).

Renaturing SDS-PAGE

Proteins were separated in SDS-PAGE using a 4% stacking gel and a 10-ml 12% separating gel containing 0.5 ml of L. monocytogenes 491 cells which had been autoclaved and concentrated 100-fold in spent BHI broth. Following electrophoresis, the gel was washed in distilled water for 10 minutes and then gently shaken in three to four changes of renaturing buffer (50 mM Tris-HCl pH 8, 100 mM NaCl and 1% Triton-X100) at 23° C. for 20 hours. The gel was then briefly rinsed with distilled water and then stained with 0.1% (wt/vol) methylene blue in 0.01% (wt/vol) KOH for 2 hours and then destained with several changes of distilled water.

Photometric Detection of L. monocytogenes Cell Wall Lytic Activity

L. monocytogenes was grown overnight in BHI and the cells were either (i) concentrated 100-fold in SM buffer and stored frozen or (ii) autoclaved and concentrated 100-fold in spent BHI and stored frozen. To test for secreted endolysin activity, supernatants (900 µl) from lactic acid bacteria grown to mid-late exponential phase were buffered by the addition of 100 µl 1M Tris-HCl (pH 8) and placed in a cuvette. L. monocytogenes substrate cells were added to the cuvette and any change in $OD_{600}$ was monitored over time at 23°.

Detection of Ply511 Secretion by Lactic Acid Bacterial Colonies on Agar Plates

To 15-ml (final volume), 0.3-ml of 100-fold concentrated autoclaved *L. monocytogenes* 491 was added to MRS or GM17 agar. Erythromycin was also added to the agar at concentrations mentioned earlier (except for the agar used to grow *L. plantarum* wild-type). Agar was buffered using 0.2 M potassium phosphate buffer pH 7 (final concentration) and the final volume was kept at 15-ml.

Killing of *L. monocytogenes* by Lactic Acid Bacteria Secreting Ply511

Lactic acid bacteria and *L. monocytogenes* QUT0085 were grown to mid-late exponential phase and the cells were harvested by centrifugation. Lactic acid bacteria were washed twice in fresh BHI broth and once in SM buffer (50 mM Tris-HCl, 100 mM NaCl, 10 mM $MgSO_4$; pH 7.5) while *L. monocytogenes* QUT0085 was washed once in BHI and once in SM buffer. Cells were resuspended at ~$10^{10}$ cells/ml for lactic acid bacteria and ~$10^9$ cells/ml for *L. monocytogenes* QUT0085. Two hundred microliters of lactic acid bacteria was added to 800 μl of SM buffer and this was then mixed with 100 μl of *L. monocytogenes* QUT0085. The mixes were incubated at 32° C. for 2.5 hours, then diluted in SM buffer and plated onto Oxford agar (Oxoid, Basingstoke, U.K.) to determine viable *L. monocytogenes* QUT0085.

Results

Cloning of the Endolysin Gene Ply511 into the Sep Secretion Cassette

Figure 5:
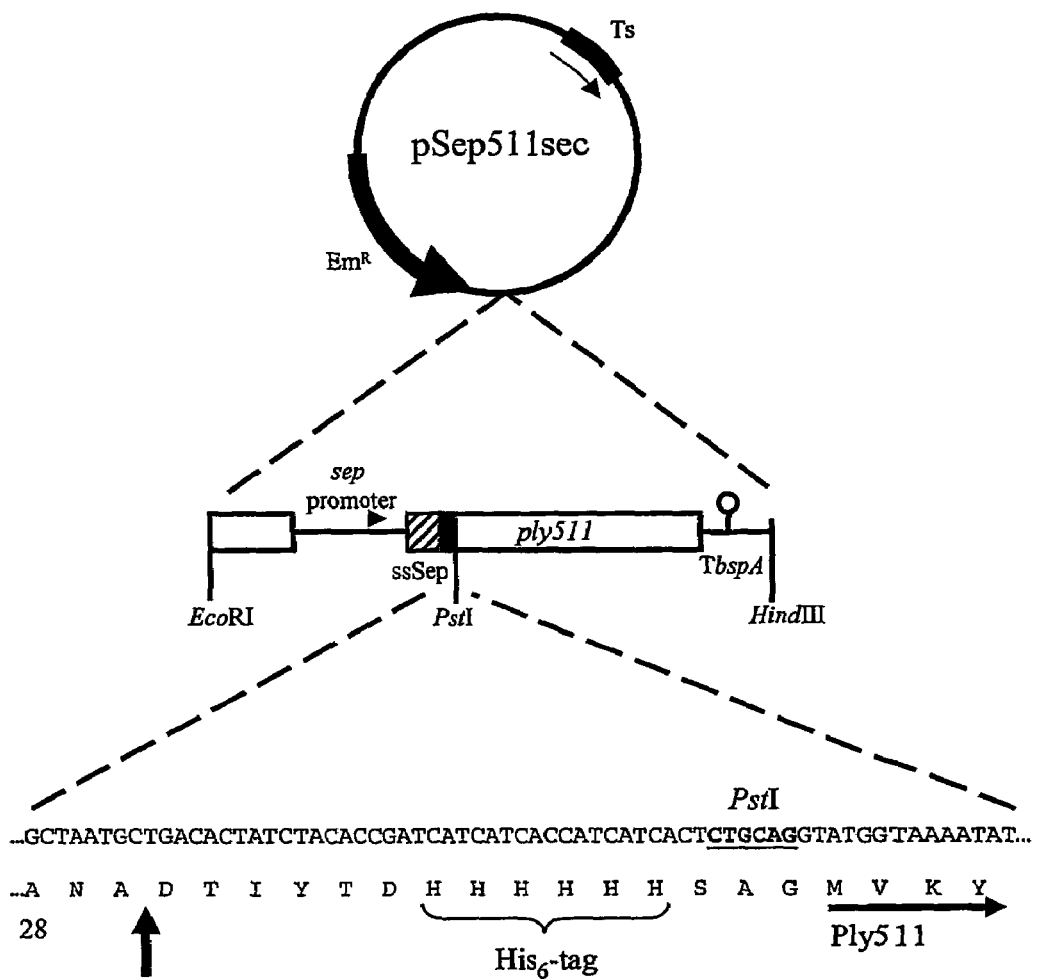
FIG. 5. Features of the pSep511 sec plasmid used for expression and secretion of Ply511 in lactic acid bacteria. The origin of the temperature sensitive origin of replication (Ts) of pGh9::ISS1 is indicated while the direction of the erythromycin resistance (Em$^R$) marker gene is also indicated by an arrow. The Sep-6×His-Ply511 expression construct cloned into pGh9::ISS1 is shown with an arrow head indicating the likely sep promoter, a hatched box indicating Sep secretion signal (ssSep), a grey box indicating the His$_6$ epitope encoding DNA and a lollipop indicating the bspA operon terminator (TbspA). At the bottom of the figure is the nucleotide and translated amino acid sequence of the junction between the Sep secretion signal and the Ply511 encoding DNA. The vertical arrow indicates the signal peptide cleavage site while the horizontal arrow indicates the start of Ply511.

DNA encoding the Ply511 endolysin of *L. monocytogenes* bacteriophage A511 was cloned in frame downstream of DNA encoding the Sep secretion signal and the sep promoter (FIG. 5). To facilitate detection of expressed proteins, a $His_6$ epitope is located between the Sep secretion signal and the start of the heterologous protein (FIG. 5). The Sep-6xHis-Ply511 construct was amplified by PCR and digested and ligated into similarly digested pGh9::ISS1. The ligation reaction was transformed into *L. lactis* and cells were plated onto GM17 including erythromycin and autoclaved *L. monocytogenes* 491 cells to detect the cell wall lytic activity of Ply511. Several transformants that had clearing zones around the colonies were harvested and their plasmids were purified. The plasmid from one of these clones was named pSep511sec.

Expression and Secretion of Ply511 in *L. fermentum* BR11, *L. rhamnosus* GG, *L. plantarum* ATCC 14917 and *L. lactis* MG1363

Figure 6:
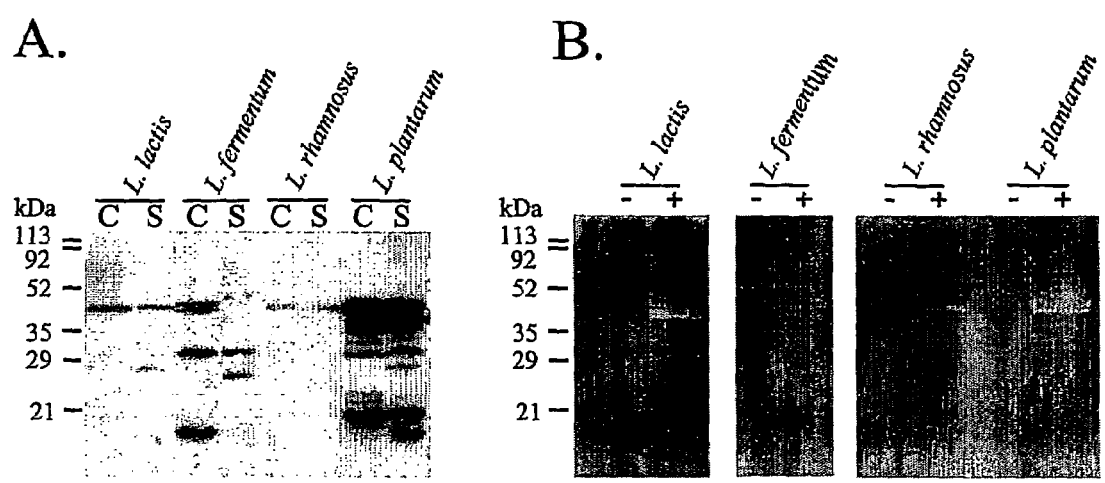
FIG. 6. Analysis of expression, secretion and activity of Ply511 produced by *Lactobacillus* spp. and *L. lactis*. (A) Western blot detection of proteins in the cell C) and supernatant (S) of lactic acid bacteria containing pSep$_5$11 sec using anti His5-HRP conjugate. The amounts of cell extract or medium loaded in each lane are the equivalent to 500 μl and 675 μl of culture, respectively. (B) Detection of bacteriolytic activity of lactic acid bacterial supenatant fractions using renaturing SDS-PAGE with autoclaved *L. monocytogenes* as the substrate. For each strain the (−) lane indicates either pGH9::ISS1 containing (*L. lactis*, *L. fermentum* and *L. rhamnosus*) or wild-type (*L. plantarum*) strains while the (+) lane idicates pSep511 sec containing strains.

The plasmid pSep511 sec was transformed by electroporation into *L. fermentum* BR11, *L. rhamnosus* GG and *L. plantarum* ATCC 14917. Cell extracts and supernatant fractions were collected from the lactobacilli and *L. lactis* transformants and were analysed by Western blotting using an anti-$His_5$-HRP conjugate. Bands were observed in all strains with the largest in each lane being ~40-kDa which is close to the calculated molecular weight of $His_6$-Ply511 (38.2-kDa) (FIG. 6A). All strains had $His_6$-Ply511 in the supernatant fraction as well as in the cell-associated fraction. All strains except *L. rhamnosus* had lower molecular weight bands indicating possible proteolytic degradation. Analysis by Western blot, *L. plantarum* produced the greatest amount of $His_6$-Ply511 and the level of full-length $His_6$-Ply 11 was estimated to be ~10 μg per liter of culture. To determine if the $His_6$-Ply511 is active, supernatants from strains containing either no plasmid, pGh9::ISS1 or pSep511sec were analysed by renaturing SDS-PAGE. Autoclaved *L. monocytogenes* 491 cells were incorporated into the separating gel and activity was identified as clear bands (FIG. 6B). Bands at ~40-kDa were observed in all supernatant fractions from strains containing pSep511sec but not in wild-type or strains containing pGh::ISS1. Extra endogenous higher molecular weight clearing bands were observed *L. lactis* (~45-kDa) and *L. fermentum* (~52 and ~70-kDa) supernatant fractions.

Activity of Ply511 Secreted by Lactic Acid Bacteria is Enhanced by Buffering with 0.2M Potassium Phosphate, pH 7

Figure 7:
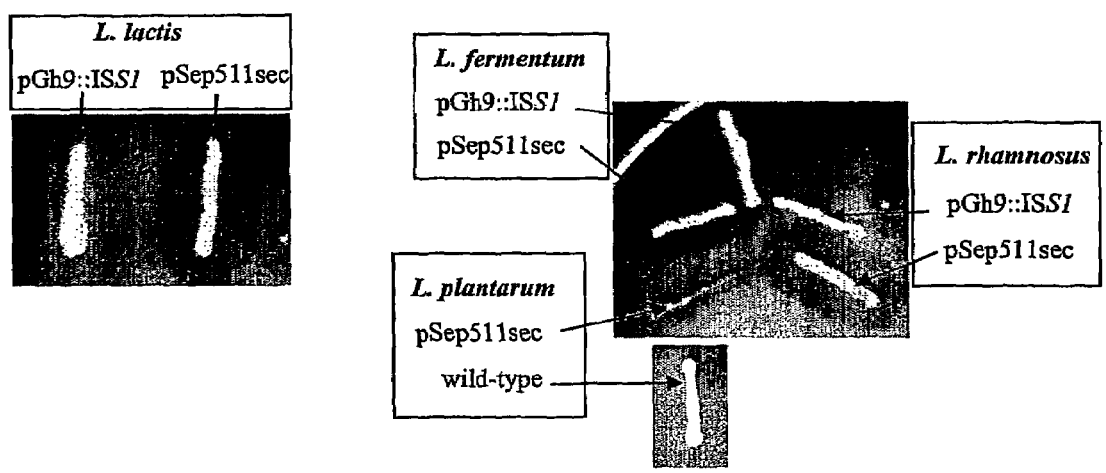
FIG. 7. Cell wall lytic activity of strains of lactic acid bacteria grown on buffered agar medium containing autoclaved *L. monocytogenes* cells. *L. lactis* were grown on buffered GM17E while *Lactobacillus* spp. strains containing plasmids were grown on buffered MRS with erythromycin while *L. plantarum* wild-type was grown on buffered MRS without erythromycin.

To determine if the lactic acid produced by lactobacilli and *L. lactis* effects Ply511 activity, we buffered the agar growth media containing autoclaved *L. monocytogenes* 491 at near neutral by the addition of 0.2 M potassium phosphate buffer (pH 7). *L. lactis* containing pSep511sec produced a small clearing zone on normal growth media and large clearing zones on buffered growth media (Table 5, FIG. 7). On normal growth media, both *L. fermentum* containing pGh9::ISS1 or pSep511sec produced the same medium sized clearing zones, while on buffered growth media only *L. fermentum* pSep511sec produced a medium clearing zone (Table 5, FIG. 7). Both *L. rhamnosus* containing pGh9::ISS1 or pSep511sec did not produce clearing zones on normal growth media, however large clearing zones were produced by *L. rhamnosus* containing pSep511sec but not by *L. rhamnosus* containing pGh9::ISS1 grown on buffered growth media (Table 5, FIG. 7). *L. plantarum* containing pSep511sec produced a small sized clearing zone while wild-type *L. plantarum* did not. On buffered growth media, *L. plantarum* containing pSep511sec produced a small clearing zone, but grew very poorly, while *L. plantarum* wild-type did not produce any clearing zone, but grew well (Table 5, FIG. 7).

A photometric activity assay was used to compare the *L. monocytogenes* cell wall lytic activity of supernatants of the lactobacilli and *L. lactis* strains expressing Ply511. Supernatants were collected from mid- to late-logarithmic growth phase, buffered by the addition of 0.1 M Tris-HCl (pH 8), mixed with *L. monocytogenes* cell suspension and any change in absorbance at 600 nm was followed. It was found using this assay that all of the supernatants of strains containing pSepPly511sec had endolysin activity. *L. plantarum* had the greatest endolysin activity while *L. lactis* and *L. rhamnosus* having moderate endolysin activity with *L. fermentum* having the least, but still detectable, endolysin activity (data not shown).

Killing of *L. monocytogenes* by lactic acid bacteria secreting Ply511 Washed *L. lactis* (~$10^9$ cells) were mixed with washed live *L. monocytogenes* QUT0085 (~$10^8$ cells) in SM buffer. After 2.5 hours, serial dilutions were plated onto Oxford agar to enumerate viable *Listeria* and GM17E to enumerate viable *L. lactis*. *L. lactis* containing pSep511sec reduced viability of *Listeria* by 1.88 log CFU/ml.

TABLE 4

| Oligonucleotide | Nucleotide sequence (5' to 3')[a] | Amplified product |
|---|---|---|
| Bam-N-term | AA<u>GGATCC</u>GAYACNATHTAYACNGTNCA[b] | sep 3' and downstream |
| pUC-Bam | CTT<u>GGATCCC</u>TGCAGGTCGACTCTAG | sep 3' or sep 5' regions |

TABLE 4-continued

| Oligonucleotide | Nucleotide sequence (5' to 3')[a] | Amplified product |
| --- | --- | --- |
| AcmA-N-term | CAGGATCCTTGATCATACTGTTGTCTTTAGC | sep 5' and upstream |
| SepUS-PCR | AATTCGCGCGAGCATCTC | entire sep locus |
| SepDS-PCR | TGCGTTTGAATTATTGTTTGC | entire sep locus |
| Nterm-US-Xba | ATATCTAGAAACCTTCCTGCTGACCT | sep 5' end and upstream |
| Nterm-Pst-US | AAACTGCAGAGTGATGATGGTGATGATGATC GGTGTA GATAGTGTCAGCA | sep 5' end and upstream |
| SepDS-PstXho | AAACTGCAGCAGGTTCTCGAGACACTATCTA CACCGTACA | sep 3' end and terminator |
| SepDS-ApaSal | CAGGGGCCCGTCGACCTATACCTGTCGAATC CA | sep 3' end and terminator |
| E-cad-PstI | AGACCTGCAGGAGACTGGGTTATTCCTCCCA | E-cadherin encoding region |
| E-cad-XhoI | AGACTCGAGGTTAATCGTTGGTGTCAGTGAC TGT | E-cadherin encoding region |

[a]Underline indicates restriction endonuclease recognition sites (SEQ ID NOS: 22-33 respectively).
[b]Y = C or T; H = A, C or T; N = A, G, C or

TABLE 5

L. monocytogenes cell wall lytic activity of lactic acid bacteria grown on agar plates with and without 0.2M potassium phosphate buffer[a].

| | Normal growth media | | Buffered growth media | |
| --- | --- | --- | --- | --- |
| | pGh9:ISS1 or wild-type | pSep511sec | pGh9::ISS1 or wild-type | pSep511sec |
| L. lactis | − | + | − | +++ |
| L. fermentum | ++ | ++ | − | ++ |
| L. rhamnosus | − | − | − | +++ |
| L. plantarum | − | + | − | +[b] |

[a]clearing zones around the colonies were scored as follows: no clearing zone (−), small just visible clearing zone (+), medium sized clearing zone (++), and large clearing zone (+++).
[b]this strain grew very poorly on buffered growth media but grew well on normal growth media.

All publications and patent applications mentioned in this specification are indicative of the level of skill of those skilled in the art to which this invention pertains. All publications and patent applications are herein incorporated by reference to the same extent as if each individual publication or patent application was specifically and individually intended to be incorporation by reference.

The invention claimed is:

1. An isolated peptide having at least 90% amino acid homology with the amino acid sequence of SEQ ID NO: 2.
2. An isolated peptide comprising the amino acid sequence of SEQ ID NO: 2.
3. The isolated peptide according to claim 2, further comprising the amino acid sequence of SEQ ID NO: 1.
4. The isolated peptide according to claim 2, further comprising the amino acid sequence of SEQ ID NO: 3.
5. The isolated peptide according to claim 2, further comprising the amino acid sequence of SEQ ID NO: 4.
6. An isolated peptide comprising the amino acid sequence of SEQ ID NO: 5.
7. An isolated peptide comprising the amino acid sequence of SEQ ID NO: 6.
8. A fusion protein comprising a peptide according to claim 2.
9. A fusion protein comprising a peptide according to claim 1.

* * * * *